US009909098B2

(12) United States Patent
Mitragotri et al.

(10) Patent No.: US 9,909,098 B2
(45) Date of Patent: Mar. 6, 2018

(54) METHODS OF TISSUE-BASED DIAGNOSIS

(75) Inventors: Samir M. Mitragotri, Santa Barbara, CA (US); Sumit Paliwal, Goleta, CA (US); Makoto Ogura, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 661 days.

(21) Appl. No.: 12/664,994

(22) PCT Filed: Aug. 6, 2008

(86) PCT No.: PCT/US2008/072384
§ 371 (c)(1),
(2), (4) Date: Jun. 29, 2010

(87) PCT Pub. No.: WO2009/048681
PCT Pub. Date: Apr. 16, 2009

(65) Prior Publication Data
US 2010/0261176 A1  Oct. 14, 2010

Related U.S. Application Data

(60) Provisional application No. 60/963,773, filed on Aug. 6, 2007.

(51) Int. Cl.
G01N 1/00 (2006.01)
A61K 9/10 (2006.01)
A61K 49/00 (2006.01)
C12M 1/33 (2006.01)
G01N 1/28 (2006.01)

(52) U.S. Cl.
CPC ............ C12M 45/02 (2013.01); G01N 1/286 (2013.01)

(58) Field of Classification Search
None
See application file for complete search history.

(56) References Cited

U.S. PATENT DOCUMENTS

| | | | |
|---|---|---|---|
| 3,962,150 A * | 6/1976 | Viola | A61K 8/44 510/137 |
| 4,268,613 A | 5/1981 | Okishi | |
| 5,398,690 A | 3/1995 | Batten et al. | |
| 5,492,126 A | 2/1996 | Hennige et al. | |
| 5,696,069 A * | 12/1997 | Ito et al. | 510/123 |
| 5,739,432 A | 4/1998 | Sinha | |
| 5,804,452 A | 9/1998 | Povonost et al. | |
| 5,913,833 A | 6/1999 | Elstrom et al. | |
| 6,004,578 A | 12/1999 | Lee | |
| 6,007,497 A | 12/1999 | Huitema | |
| 6,093,551 A | 7/2000 | Raithel et al. | |
| 6,165,500 A | 12/2000 | Cevic | |
| 6,190,315 B1 * | 2/2001 | Kost | A61M 37/0092 600/309 |
| 6,328,728 B1 | 12/2001 | Holladay et al. | |
| 6,544,211 B1 | 4/2003 | Andrew et al. | |
| 6,560,478 B1 | 5/2003 | Alfano et al. | |
| 6,589,173 B1 | 7/2003 | Mitragotri | |
| 2002/0082518 A1 | 6/2002 | Weiss et al. | |
| 2002/0188280 A1 | 12/2002 | Nguyen et al. | |
| 2003/0060818 A1 | 3/2003 | Kannenberg et al. | |
| 2003/0143116 A1 | 7/2003 | Zheng et al. | |
| 2003/0211520 A1 | 11/2003 | Afar et al. | |
| 2004/0151745 A1 | 8/2004 | Zimmer et al. | |
| 2004/0191854 A1 | 9/2004 | Lapen et al. | |
| 2005/0164903 A1 | 7/2005 | Ko et al. | |
| 2005/0214825 A1 * | 9/2005 | Stuelpnagel | 435/6 |
| 2006/0046261 A1 | 3/2006 | Porter et al. | |
| 2006/0100569 A1 | 5/2006 | McRury et al. | |
| 2006/0116563 A1 | 6/2006 | Asano et al. | |
| 2006/0165823 A1 * | 7/2006 | Herrera | 424/757 |
| 2006/0166222 A1 * | 7/2006 | Lu et al. | 435/6 |
| 2007/0055181 A1 | 3/2007 | Deem et al. | |
| 2007/0055261 A1 | 3/2007 | Reiley et al. | |
| 2007/0059268 A1 * | 3/2007 | Magee | 424/70.21 |
| 2007/0059687 A1 | 3/2007 | Ohno et al. | |
| 2007/0173448 A1 | 7/2007 | Shah et al. | |
| 2007/0183936 A1 | 8/2007 | Newsam et al. | |
| 2007/0269379 A1 | 11/2007 | Mitragotri et al. | |
| 2008/0003575 A1 | 1/2008 | Michalik et al. | |
| 2008/0200545 A1 * | 8/2008 | Aubrun-Sonneville et al. | 514/557 |
| 2010/0261176 A1 | 10/2010 | Mitragotri et al. | |

FOREIGN PATENT DOCUMENTS

EP 0743519 A2 11/1996
JP 2005336241 A 12/2005
WO WO 2005/009510 * 2/2005

OTHER PUBLICATIONS

Tutulan-Cunita (Genes to cells (2005) vol. 10, pp. 409-420).*
Pubchem polidocanol (pubchem.ncbi.nlm.nih.gov/summary/summary.cgi?cid=24750&loc=ec_rcs, downloaded Oct. 29, 2012 ).*
Ayliffe ( Journal of Hospital infection (1988) vol. 11m pp. 226-243).*
Sugimura et al., Transgenic patchouli plants produced by Agrobacterium-mediated transformation. Plant Cell, Tissue and Organ Culture (2005) 82: 251-257.*
Zanten et al., Cerebrospinal fluid tumour markers in patients treated for meningeal malignancy. Journal of Neurology, Neuro$urgtry, and Prychialry 1991;S4:119-123.*

(Continued)

Primary Examiner — Scott Long
Assistant Examiner — Arthur S Leonard
(74) Attorney, Agent, or Firm — Pabst Patent Group LLP

(57) ABSTRACT

The current invention provides methods, as well as compositions useful in such methods, involving application of energy to a tissue of interest to generate a liquefied sample comprising tissue constituents so as to provide for rapid tissue sampling, as well as qualitative and/or quantitative detection of analytes that may be part of tissue constituents (e.g., several types of biomolecules, drugs, and microbes). Determination of tissue composition can be used in a variety of applications, including diagnosis or prognosis of local as well as systemic diseases, evaluating bioavailability of therapeutics in different tissues following drug administration, forensic detection of drugs-of-abuse, evaluating changes in the tissue microenvironment following exposure to a harmful agent, and various other applications.

19 Claims, 12 Drawing Sheets

(56) References Cited

OTHER PUBLICATIONS

Guenthner et al., Gram-negative bacilli as nontransient flora on the hands of hospital personnel. J. Clin. Microbiol. 1987, 25(3):488.*
Malminen et al., Functional expression of NF1 tumor suppressor protein: association with keratin intermediate filaments during the early development of human epidermis. BMC Dermatology 2002, 2:10, p. 1-11.*
Harmon Stores Product Sheet, Calamine Lotion, www.harmondiscount.com/072785104167.html, Feb. 1, 2001, p. 1.*
Prasanthi et al., Effect of Chemical Enhancers in Transdermal Permeation of Alfuzosin Hydrochloride. ISRN Pharmaceutics, vol. 2012, pp. 1-8.*
Sakai et al., Contribution of Calcium Ion Sequestration by Polyoxyethylated Nonionic Surfactants to the Enhanced Colonic Absorption of pAminobenzoic Acid . Journal of Pharmaceutical Sciences : pp. 387-390, vol. 75, No. 4, Apr. 1986.*
Huang et al., "Separation and measurement of desmosine and isodesmosine in vascular tissue hydrolysates by micellar electrokinetic capillary chromatography with a mixed micelle system", J. Chromaography A 1175 : 294-296 (2007).
Written Opinion and International Search Report of the International Searching Authority from related PCT Application No. PCT/US08/72384.
Ayliffe, et al. "Hand disinfection: a comparison of various agents in laboratory and ward studies" J. Hospital Infection, 1988, 11, 226-243.
Harmon Stores Product Sheet, Calamine Lotion: www.harmondiscount.com, Feb. 2, 2001.
Detergent Selection Table, accessed Jun. 20, 2016: http://www.science.co.il/Biomedical/detergent_selection_table.pdf.

* cited by examiner

FIG. 9: Cytokine Profile of Atopic Dermatitis skin

Interleukins

| Name | Enhancement | p value | |
|---|---|---|---|
| IL-4 | 0.09 | 0.005 | ** |
| IL-6 | 3.03 | 0.027 | ** |
| IL-3 | 2.41 | 0.000 | ** |
| IL-1a | 1.92 | 0.021 | ** |
| IL-5 | 1.65 | 0.005 | ** |
| IL-9 | 1.64 | 0.023 | ** |
| IL-1b | 1.70 | 0.098 | * |
| IL-12 p40/p70 | 1.61 | 0.384 | |
| IL-2 | 1.54 | 0.190 | |
| IL-13 | 1.21 | 0.504 | |
| IL-12 p70 | 1.15 | 0.378 | |
| IL-10 | 1.12 | 0.764 | |
| IL-17 | 0.05 | 0.014 | ** |

Chemokines

| Name | Enhancement | p value | |
|---|---|---|---|
| TCA-3 | 2.45 | 0.004 | ** |
| TARC | 2.35 | 0.004 | ** |
| TECK | 2.23 | 0.000 | ** |
| CRG-2 | 1.75 | 0.003 | ** |
| RANTES | 1.70 | 0.008 | ** |
| CTACK | 1.66 | 0.000 | ** |
| Eotaxin-2 | 1.61 | 0.032 | ** |
| CXCL-16 | 1.50 | 0.005 | ** |
| MIP-1a | 1.34 | 0.009 | ** |
| MCP-1 | 1.34 | 0.015 | ** |
| MIP-2 | 1.22 | 0.038 | ** |
| MIP-1g | 1.66 | 0.099 | * |
| PF-4 | 1.44 | 0.064 | * |
| MIP-3a | 1.27 | 0.094 | * |
| Fractalkine | 1.72 | 0.210 | |
| LIX | 1.71 | 0.066 | |
| Lymphotactin | 1.26 | 0.403 | |
| BLC | 1.09 | 0.585 | |
| MIP-3 b | 1.06 | 0.925 | |
| SDF-1a | 0.68 | 0.635 | |
| KC | 0.68 | 0.598 | |
| MIG | 0.41 | 0.175 | |
| MCP-5 | 0.42 | 0.047 | ** |

Colony Stimulating Factors

| Name | Enhancement | p value | |
|---|---|---|---|
| M-CSF | 1.96 | 0.006 | ** |
| GM-CFS | 1.75 | 0.183 | |
| G-CSF | 1.67 | 0.166 | |

Growth factors

| Name | Enhancement | p value | |
|---|---|---|---|
| IGFBP-3 | 3.12 | 0.000 | ** |
| IGFBP-5 | 1.76 | 0.722 | |
| TPO | 1.61 | 0.217 | |
| IGFBP-6 | 1.35 | 0.253 | |
| VEGF | 0.59 | 0.698 | |
| Leptin | 0.26 | 0.113 | |

Others

| Name | Enhancement | p value | |
|---|---|---|---|
| IL-3Rb | 2.22 | 0.001 | ** |
| Leptin R | 2.07 | 0.012 | ** |
| CD30L | 2.06 | 0.054 | * |
| CD30 T | 1.69 | 0.094 | * |
| P-selectin | 1.57 | 0.052 | * |
| sTNF RII | 4.53 | 0.497 | |
| sTNF R1 | 3.02 | 0.149 | |
| Fas ligand | 2.08 | 0.060 | |
| L-selectin | 1.52 | 0.169 | |
| Axl | 1.36 | 0.550 | |
| VCAM-1 | 1.29 | 0.194 | |
| CD40 | 1.12 | 0.769 | |
| TNFa | 1.09 | 0.492 | |
| IFNg | 0.94 | 0.830 | |
| TIMP-1 | 0.15 | 0.005 | ** |

(** and * represents a value of $p < 0.05$ and $p < 0.1$ in student's t test respectively)

FIG. 10: Cytokine profile of Psoriasis skin

Interleukins

| Name | Enhancement | p value | |
|---|---|---|---|
| IL-4 | 2.50 | 0.006 | ** |
| IL-3 | 1.98 | 0.002 | ** |
| IL-1a | 1.35 | 0.019 | ** |
| IL-9 | 1.19 | 0.035 | ** |
| IL-5 | 1.69 | 0.098 | * |
| IL-6 | 2.35 | 0.115 | |
| IL-10 | 1.51 | 0.354 | |
| IL-1b | 1.14 | 0.486 | |
| IL-12 p70 | 1.12 | 0.185 | |
| IL-2 | 0.99 | 0.963 | |
| IL-13 | 0.94 | 0.775 | |
| IL-12 p40/p70 | 0.84 | 0.720 | |
| IL-17 | 0.34 | 0.155 | |

Chemokines

| Name | Enhancement | p value | |
|---|---|---|---|
| TECK | 1.64 | 0.047 | ** |
| CRG-2 | 1.57 | 0.014 | ** |
| LIX | 1.58 | 0.004 | ** |
| MIP-3b | 1.36 | 0.004 | ** |
| CTACK | 1.35 | 0.010 | ** |
| RANTES | 1.34 | 0.006 | ** |
| TCA-3 | 1.75 | 0.059 | * |
| MIP-1a | 1.40 | 0.166 | |
| Fractalkine | 1.39 | 0.294 | |
| MIP-1g | 1.37 | 0.160 | |
| TARC | 1.14 | 0.343 | |
| CXCL 16 | 1.07 | 0.650 | |
| Eotaxin-2 | 1.06 | 0.595 | |
| MCP1 | 1.04 | 0.738 | |
| BLC | 0.96 | 0.759 | |
| MIP-3 b | 0.91 | 0.707 | |
| PF-4 | 0.91 | 0.253 | |
| MIG | 0.73 | 0.739 | |
| KC | 0.72 | 0.649 | |
| Lymphotactin | 0.72 | 0.202 | |
| MIP-2 | 0.86 | 0.096 | * |
| SDF-1a | 0.00 | 0.071 | * |
| MCP-5 | 0.04 | 0.000 | ** |

Colony Stimulating Factors

| Name | Enhancement | p value | |
|---|---|---|---|
| G-CSF | 1.51 | 0.029 | ** |
| M-CSF | 1.10 | 0.380 | |
| GM-CSF | 1.08 | 0.826 | |

Growth Factors

| Name | Enhancement | p value | |
|---|---|---|---|
| IGFBP-3 | 2.79 | 0.000 | ** |
| IGFBP-6 | 1.21 | 0.072 | * |
| IGFBP-5 | 10.30 | 0.354 | |
| VEGF | 4.83 | 0.342 | |
| TPO | 0.98 | 0.910 | |
| Leptin | 0.21 | 0.094 | * |

Others

| Name | Enhancement | p value | |
|---|---|---|---|
| CD30L | 1.72 | 0.031 | ** |
| IL-3Rb | 1.57 | 0.044 | ** |
| Leptin R | 1.49 | 0.003 | ** |
| Fas ligand | 2.59 | 0.093 | * |
| L-selectin | 1.35 | 0.056 | * |
| IFNg | 1.99 | 0.222 | |
| Axl | 1.60 | 0.373 | |
| TNFa | 1.24 | 0.481 | |
| VCAM-1 | 1.04 | 0.825 | |
| P-selectin | 1.02 | 0.928 | |
| CD30 T | 1.01 | 0.903 | |
| CD40 | 0.66 | 0.439 | |
| sTNF R1 | 0.63 | 0.490 | |
| sTNF RII | 0.00 | 0.391 | |
| TIMP-1 | 0.00 | 0.002 | ** |

(** and * represents a value of $p < 0.05$ and $p < 0.1$ in student's $t$ test respectively)

FIG. 11: Lipid profiles of Atopic Dermatitis and Psoriasis

| Lipids | Atopic Dermatitis | Psoriasis |
|---|---|---|
| | Enhancement | Enhancement |
| Squalene | 0.41 * | 0.57 * |
| Cholesteryl esters | 0.22 | 0.27 |
| UN2 | 0.64 | 0.63 |
| UN1 | 1.04 | 1.28 * |
| Methyl Oleate | 1.22 | 1.32 |
| Triglycerides | 3.47 | 1.76 |
| Cholesteryl diesters | 1.46 | 1.59 |
| Free fatty acids | 1.21 | 1.55 |
| Lanosterol | 0.96 | 1.30 |
| Cholesterol | 1.52 | 2.48 |
| Polar Lipids | 1.45 * | 1.49 * |

(* represents a value of $p < 0.05$ in student's t test)

METHODS OF TISSUE-BASED DIAGNOSIS

CROSS REFERENCE TO RELATED APPLICATION

This application claims the benefit of U.S. Provisional Patent Application No. 60/963,773 filed Aug. 6, 2007, which application is incorporated herein by reference in its entirety.

GOVERNMENT RIGHTS

This invention was made with government support under federal grant nos. W81XWH-06-1-0400 awarded by the United States Army. The United States Government has certain rights in this invention.

BACKGROUND

The biomolecular composition of human tissues, represented by a multitude of lipids, proteins, nucleic acids, and other miscellaneous molecules, is a sensitive indicator of local pathologies, such as cancer, allergies, and eczema, as well as several systemic diseases, such as cardiovascular disease, Alzheimer's disease, and diabetes. In addition, tissue molecular composition also holds critical information about the body's exposure to exogenous chemical and biological entities. However, this information is not currently used in diagnostic methods due to a lack of patient-friendly and standardized methods for routine sample collection from tissues. Instead, clinical diagnosis is invariably performed by visual observation and histopathological analysis of tissue biopsies, which are highly limited due to their qualitative nature, leading to increased misdiagnosis and inappropriate use. In addition to being invasive, current methods also fall short in explaining a complete molecular genesis of diseases, and fail to distinguish between diseases.

Prior approaches using physical and chemical methods for assessing tissue fluid have focused chiefly on extracting a few molecules that are freely present in the interstitial fluid, such as calcium and glucose. Use of tape stripping for physically harvesting superficially-lying tissue constituents with an adhesive tape has been reported; however this technique has been shown to be limited by inefficacy, lack of a standardized protocol, and high heterogeneity in tissue sampling.

SUMMARY

The current invention provides methods, as well as compositions useful in such methods, involving application of energy to a tissue of interest to generate a liquefied sample comprising tissue constituents so as to provide for rapid tissue sampling, as well as qualitative and/or quantitative detection of analytes that may be part of tissue constituents (e.g., several types of biomolecules, drugs, and microbes). Determination of tissue composition can be used in a variety of applications, including diagnosis or prognosis of local as well as systemic diseases, evaluating bioavailability of therapeutics in different tissues following drug administration, forensic detection of drugs-of-abuse, evaluating changes in the tissue microenvironment following exposure to a harmful agent, and various other applications.

The current disclosure provides methods for generating a liquefied tissue sample from a subject. The method involves applying energy and a liquefaction promoting medium to a tissue of interest of a subject, the applying producing a liquefied tissue sample, and collecting the liquefied tissue sample. In some embodiments, the method involves analyzing the presence or absence of at least one analyte in the liquefied tissue sample, wherein the analysis facilitates diagnosis of a condition of interest. In certain embodiments, the analysis involves generating an analyte profile from the liquefied tissue sample and comparing the analyte profile to a reference analyte profile, wherein the comparing facilitates diagnosis of a condition of interest.

In some embodiments, the liquefaction agent comprises one or more of a protease inhibitor, an RNase inhibitor, or a DNase inhibitor. In certain embodiments, the liquefaction promoting agent comprises at least one of free radical scavenger, a defoaming agent, and a protein stabilizer. In certain embodiments, the liquefaction promoting agent comprises at least one of Brij-30, N-lauroyl sarcosine, Triton X-100, Sodium Dodecyl Sulfate, DMSO, fatty acids (e.g., both saturated and unsaturated fatty acids, (e.g., Hexanoic acid, Octanoic acid, Decanoic acid, Dodecanoic acid, Palmitic acid, Stearic acid, Oleic acid, Linoleic acid, Linolenic acid, Cholic acid.)), azone and azone-like compounds (e.g., n-lauryl caprolactam, laurocapram, tranzone, Methyl pyrrolidone, Cyclohexyl pyrrolidone, Octyl pyrrolidone, Decyl pyrrolidone, Decyl methylpyrrolidone, Methyl piperazine, Phenyl piperazine, Octanamide, Hexadecanamide, Caprolactam), EDTA, or sodium hydroxide. In certain embodiments, the liquefaction promoting agent comprises a suspension of abrasive particles. In certain embodiments, the abrasive particles comprise silica or aluminum oxide.

In some embodiments, the energy is applied in the form of ultrasound, mechanical, optical, thermal, or electrical energy. In certain embodiments, the mechanical energy is applied by an abrasive material. In certain embodiments, the thermal energy is applied in the form of radio frequency energy. In certain embodiments, the optical energy is applied in the form of a laser.

In some embodiments, the liquefied tissue sample is generated for each of a healthy tissue of interest of the subject and a suspected diseased tissue of interest of the subject, and the analysis comprises comparing analytical results from the healthy tissue sample with analytical results from the suspected diseased tissue sample, wherein the comparing facilitates diagnosis of a condition of interest. In some embodiments, the liquefied tissue sample is generated for multiple tissue sites and the analysis comprises comparing analytical results from the multiple tissue sites, wherein said comparing facilitates diagnosis of a condition of interest. In some embodiments, the liquefied tissue sample is collected from multiple tissue sites, and the samples are combined to make a diagnosis.

In some embodiments, the liquefied tissue sample is collected by aspiration. In certain embodiments, the collecting is by retaining the liquefaction agent in a housing placed in contact with the tissue.

In some embodiments, the method involves detecting certain tissue constituents in the liquefied tissue sample prior to analysis of an analyte of interest, such as a disease marker. In certain embodiments, the detecting is by electrochemical, biochemical, or optical methods.

In some embodiments, the energy is applied to a tissue in the form of ultrasound with a mechanical index between 0.1 and 50. In certain embodiments, the energy is applied by contacting the tissue with a moving abrasive surface. In certain embodiments, the energy is applied to the tissue by contacting the tissue with a moving brushing device comprising a plurality of bristles. In certain embodiments, the energy is applied to the tissue by mechanized stirring of the liquefaction agent. In certain embodiments, the energy is applied to the tissue by contacting the tissue with a high velocity jet comprising a fluid mixture of abrasive particles.

In some embodiments, the tissue comprises breast, prostate, eye, vagina, bladder, nail, hair, colon, testicles, ovaries, or intestine. In certain embodiments, the tissue comprises skin or a mucosal membrane. In certain embodiments, the tissue comprises lung, brain, pancreas, liver, heart, bone, kidney, carotid artery, or aorta wall.

In some embodiments, the analyte comprises a small molecule, a drug or metabolite thereof, a polypeptide, a lipid, a nucleic acid, or a microbe. In certain embodiments, the analyte comprises an antibody, a cytokine, an illicit drug, or a cancer biomarker.

In some embodiments, the liquefied tissue sample is held in a container, and the analyte profile is generated by integrating the liquid container with one or more analytical devices. In certain embodiments, the method involves measuring the concentration of a calibrator analyte to provide a means for calibrating the analysis of the analyte.

In some embodiments, the method involves diagnosing allergic disease in a subject, and the method comprises analyzing the liquefied tissue sample for the presence or absence of IgE, wherein the analysis facilitates diagnosis of allergic disease in the subject.

In some embodiments, the method involves diagnosing cancer in a subject, and the method comprises analyzing the liquefied tissue sample for the presence or absence of one or more cancer markers, wherein the analysis facilitates diagnosis of cancer in the subject. In certain embodiments, the tissue of interest is breast, colon, vagina, nose, prostate, skin, testicle, intestine, ovary, kidney, thyroid, or mouth.

In some embodiments, the method involves diagnosing heart disease in a subject, and the method comprises analyzing the liquefied tissue sample for the presence or absence of one or more of cholesterol, triglycerides, lipoproteins, free fatty acids, and ceramides, wherein the analysis facilitates diagnosis of heart disease in the subject.

In some embodiments, the method involves detecting the presence of an illicit drug, or metabolite thereof, in a subject, and the method comprises analyzing the liquefied tissue sample for the presence or absence of an illicit drug, or metabolites thereof, wherein the analysis provides for detection of illicit drugs in the subject.

In some embodiments, the method involves detecting a microorganism in a subject, and the method comprises applying energy and a coupling medium to a tissue of interest in a subject and analyzing the coupling medium for the presence or absence of a microorganism, wherein the analysis provides for detection of the presence or absence of a microorganism.

The present disclosure also provides a medium comprising a nonionic surfactant (e.g., selected from a Brij series surfactant, a Triton-X surfactant, and a Sorbitan surfactant); an anionic surfactant (e.g., a sarcosine surfactant); and a hydrophilic solvent, where the medium has a total concentration of the nonionic surfactant and the sarcosine surfactants from about 0.5% to 10% (w/v).

In related embodiments, the medium is in a container adapted for use with an energy application device. The container can comprise one or more sensors for monitoring one or more of temperature, pH, optical property, and electrical property of the medium.

In related embodiments, the total surfactant concentration of the medium is about 1% (w/v). The nonionic surfactant can be, for example, Brij 30 and the sarcosine surfactant can be, for example, N-lauroyl sarcosine. In further embodiments the nonionic surfactant (e.g., Brij 30) and the anionic surfactant (e.g., a sarcosine surfactant, e.g., N-lauroyl sarcosine) are present at a ratio of is 50:50.

In one embodiment, the medium comprises solubilized tissue constituents, and/or can comprise one or more of a fatty acid, an azone-like molecule, a chelating agent, and an inorganic compound. The medium can comprise, in some embodiments, abrasive particles.

The present disclosure also provides methods of obtaining a sample, the method comprising applying energy and the medium of claim 40 to a tissue of interest in a subject; and analyzing the medium for the presence or absence of an analyte; where the analysis provides for detection of the presence or absence of the analyte.

These and other features of the invention will become apparent to those persons skilled in the art upon reading the details of the method of tissue-based diagnosis as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 9 shows a typical cytokine profile of Atopic Dermatitis skin.

FIG. 10 shows a typical cytokine profile of Psoriasis skin.

FIG. 11 shows a typical lipid profile of Atopic Dermatitis skin and Psoriasis skin.

DEFINITIONS

Figure 1A:
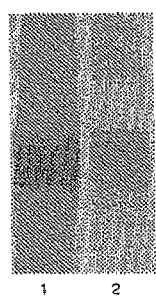
FIG. 1 (Panels a-j) is a collection of photographs and a graph illustrating: characterization of various analytes that were liquefied from porcine or human skin using different techniques. The data show solubilized proteins that were liquefied from porcine skin and analyzed by SDS-PAGE (Panel a); characterization of solubilized proteins that were liquefied from human skin using SDS-PAGE (Panel b); Western blot analysis of keratins liquefied from pig skin (Panel c); Western blot analysis of keratins liquefied from human skin (Panel d); Western blot analysis of heat shock family protein—hsp60 from porcine skin (Panel e); Western blot analysis of heat shock family protein—hsp70 from porcine skin (Panel f); Western blot analysis of β-actin from porcine skin (Panel g); thin layer chromatography comparing non-polar lipids that were liquefied from pig stratum corneum homogenate with non-polar lipids that were ultrasound liquefied from porcine skin (Panel h); thin layer chromatography comparing polar lipids that were liquefied from pig stratum corneum homogenate with polar lipids that were ultrasound liquefied from porcine skin (Panel i); and a graph comparing the relative composition profile of free amino acids in ultrasound liquefied and in homogenized porcine stratum corneum (Panel j). In Panel h and Panel i, several biomolecules are abbreviated as: paraffin hydrocarbons (PH), squalene (SQ), cholesteryl esters (CE), triglycerides (TG), cholesteryl diesters (CD), free fatty acids (FA), cholesterol (CH), lanosterol (LA), ceramide 1-6 (C1-6), and Glucosyl-/Phospho-lipids (OP).
Figure 1B:
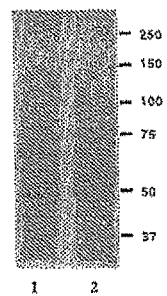
Figures 1H, 1I:
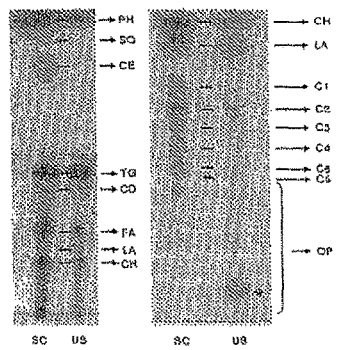
Figure 1C:
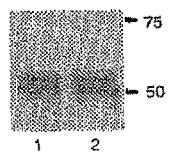
Figure 1D:
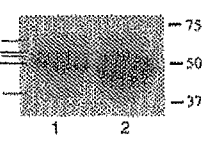
Figure 1E:
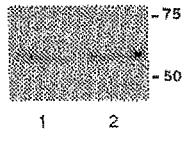
Figure 1F:
Figure 1G:
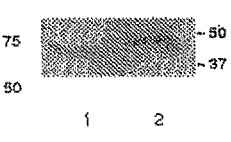
Figure 1J:
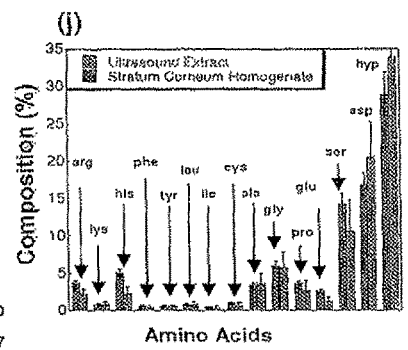

"Energy" as used herein means any appropriate energy that can be applied to tissue to accomplish the objective of the methods disclosed herein (e.g., liquefying tissue). Exemplary types of energy include mechanical energy (e.g., abrasion, shear, vacuum, pressure, suction), ultrasound, optical (e.g., laser), thermal, and electrical energy.

An "analyte" as used herein means any biomolecule (e.g., polypeptide, nucleic acid, lipid, and the like), drug (e.g., therapeutic drugs, drugs-of-abuse, metabolites, and the like), small molecule (e.g., natural moisturizing factors, nicotine, and the like, with the understanding that small molecules can also be drugs), warfare agent, environmental contaminant (e.g., pesticides, etc.), microbe (e.g., bacterium, virus, fungus, yeast, and the like) and the like that is present in or on the tissue and can be extracted from the tissue of interest (e.g., skin, a mucosal membrane, and the like) and detected, analyzed, and/or quantified.

The term "liquefaction" is used to describe the process by which tissue and/or tissue constituents are converted to a liquid state through exposure to sufficient energy and, optionally, a liquefaction promoting medium, and can involve conversion of at least a portion of a tissue structure of interest to a liquid form. A tissue sample that has been subjected to liquefaction as sometimes referred to herein as a "liquefied" sample.

The term "liquefaction-promoting medium" (LPM) is used to describe a substance that facilitates solubilization of one or more tissue constituents, and can facilitate conversion of at least a portion of a tissue structure into a liquid when exposed to energy.

The term "liquefaction-promoting agent" (LPA) is used to describe a component of the liquefaction promoting medium, particularly an agent that promotes at least solubilization and/or preservation of bioactivity of one or more tissue constituents.

A "calibration analyte" as used herein means any molecule naturally present in a tissue of interest at a known concentration, which can serve as a reference analyte (e.g., as a positive control to ensure a desired degree of liquefaction was achieved).

A "biomolecule" as used herein means any molecule or ion which has a biological origin or function. Non-limiting examples of biomolecules include proteins (e.g., disease biomarkers such as cancer biomarkers, antibodies: IgE, IgG, IgA, IgD, or IgM, and the like), peptides, lipids (e.g., cholesterol, ceramides, or fatty acids), nucleic acids (RNA and DNA), small molecules (e.g., glucose, urea, creatine), small molecule drugs or metabolites thereof, microbes, inorganic molecules, elements, or ions (e.g., iron, $Ca^{2+}$, $K^+$, $Na^+$, and the like). In some embodiments, the biomolecule is other than glucose and/or is other than a cancer marker.

The term "abused drug" or "drug-of-abuse" or "illicit drug" are used interchangeably herein to refer to any substance which is regulated by a governmental (e.g. federally or state regulated) of which presence in a human tissue, and/or presence above a certain level in a human tissue, is illegal or can be harmful to a human being. Examples of abused drugs include: cocaine, heroin, methyl amphetamine, and prescription drugs taken in excess of dosage, or taken without a prescription (e.g., painkillers such as opioids).

The term "warfare agent" as used herein refers to any molecule, compound, or composition of either biological or chemical origin that may be used as a weapon. Examples of warfare agents include nerve gases (e.g. VX, Sarin), phosgene, toxins, spores (e.g., anthrax), and the like.

The term "environmental contaminant" as used herein includes any molecule, compound, or composition which can be detrimental to an individual, e.g., when at concentrations elevated above a risk threshold. Examples include water pollutants (e.g., fertilizers, pesticides, fungicides, insecticides, herbicides, heavy metals, halides), soil pollutants (e.g., fertilizers, pesticides, fungicides, insecticides, herbicides, heavy metals, halides), air pollutants (e.g., $NO_x$, $SO_x$, greenhouse gases, persistent organic pollutants (POPs), particulate matter, smog).

The term "natural moisturizing factor" (NMFs) as used herein means any one of several types of small molecules, including but not limited to free amino acids, lactate, and urea, which are derivatives of fillagrin. NMFs can be used as analytes to facilitate assessment of general skin health (e.g., dry skin, flaky skin, normal skin, etc.).

The term "mechanical index" as used herein means the ratio of the amplitude of peak negative pressure in an ultrasonic field and the square-root of the ultrasound frequency (Mechanical Index=(Pressure (MPa))/(Frequency (MHz))$^{0.5}$.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a tissue" includes a plurality of such tissues and reference to "the liquid" includes reference to one or more liquids, and so forth. It is further noted that the claims may be drafted to exclude any optional element. As such, this statement is intended to serve as antecedent basis for use of such exclusive terminology as "solely," "only," and the like, in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

The current invention provides methods, as well as compositions useful in such methods, involving application of energy to a tissue of interest to generate a liquefied sample comprising tissue constituents so as to provide for rapid tissue sampling, as well as qualitative and/or quantitative detection of analytes that may be part of tissue constituents (e.g., several types of biomolecules, drugs, and microbes). Determination of tissue composition can be used in a variety of applications, including diagnosis or prognosis of local as well as systemic diseases, evaluating bioavailability of therapeutics in different tissues following drug administration, forensic detection of drugs-of-abuse, evaluating changes in the tissue microenvironment following exposure to a harmful agent, and various other applications.

Energy Application Devices

The methods disclosed herein can be generally carried out using a device having an energy source operably coupled to a reservoir, where the reservoir houses a medium in which analytes are collected and which, in most embodiments, facilitates transfer of energy to the tissue of interest and can thus, where desired, facilitate liquefaction of a tissue sample. The reservoir housing is adapted for use with the energy source, and can optionally be provided as a container separate from the energy application device.

For example, the reservoir housing can include connectors for attachment to an electrical energy device, and can be optionally fluidly coupled to a source of LPM that may be provided as an element of an energy application device or may be external to the energy application device. The reservoir housing can also be provided as a separate container that is configured to receive an energy application device such that in use the energy application device provides for transmission of energy to a tissue of interest through LPM contained in the reservoir housing. The reservoir housing can optionally include operably positioned sensors to provide for monitoring of one or more feedback parameters as exemplified herein. The reservoir housing can be made of any suitable material compatible for use with the selected LPM, energy application device, and tissue of interest that will be the subject of analysis.

In use, the reservoir housing is placed in contact with the subject's tissue to make contact between the medium and the tissue, and the energy source is activated. In certain embodiments, energy may be applied directly to the tissue before the medium is placed in contact with the tissue. The device can be operably coupled to additional energy sources, (e.g., ultrasound, suction or pressure), which are adapted for use with the primary energy source and reservoir housing, and can also be applied to the tissue to facilitate transfer of energy to the tissue. As energy is applied to the tissue, constituents of the tissue are dislodged by the energy and collected in the medium. The reservoir housing can be operably coupled to a detection device that can quantitatively measure the tissue constituents present in the medium, and which is adapted for use with the energy source and reservoir housing. The reservoir housing can also be equipped with one or more sensors for use in monitoring a feedback parameter of the tissue or the medium (e.g., a temperature, chemical (e.g., pH), optical, and/or electrical sensor).

Energy can be applied to the tissue from a single energy source or as a combination of sources. Exemplary energy sources include mechanical (e.g., abrasion, shear, vacuum, pressure, and the like), ultrasound, optical (e.g., laser), thermal, and electrical energy. The intensity of the energy applied, as well as the duration of the energy application, may be appropriately adjusted for the particular tissue of interest and the particular application of the method. The energy intensity and duration of application may also be appropriately adjusted based on the particular liquefaction promoting medium (LPM) used in connection with the energy. In some embodiments, an energy exposure time of greater than 1 minute, greater than 90 seconds, or greater than 2 minutes is provided in order to produce a suitable liquefied tissue sample. The magnitude of energy depends on the analyte of interest and the selection of LPM. Energy can be applied to the tissue before application of the LPM, or in the presence of the LPM. Higher energies are required to liquefy tissues in the absence of surfactants or particles in the LPM. Use of high energies is limited by their adverse effects on the tissue or its constituents. A significant adverse effect is attributed to temperature elevation in the tissue, also known as thermal effects. In some embodiments, therefore, it might be necessary to incorporate a temperature sensing element (e.g., a thermocouple) in this method that allows monitoring of the temperature of the tissue and/or the LPM, facilitating the judgment of a safe amount of energy exposure to the tissue. The necessary energy level is significantly reduced by appropriate selection of LPM. For example, use of saline alone along with ultrasound resulted in recovery of less than 0.1 mg protein per $cm^2$ of skin. On the other hand, incorporation of NLS and Brij-30 at a concentration of 1% w/v in LPM increased protein recovery to more than 0.6 mg per $cm^2$ of skin.

In certain embodiments, energy can be applied to a tissue using an energy delivery chamber that includes an energy producing element. The chamber, when placed on the tissue, will expose the tissue to the energy producing element and allow energy to be applied to the tissue with minimal interference. Such a chamber can contain LPM and provide for contact of the LPM with the tissue such that, upon application of energy, tissue constituents can be directly collected into the solution.

In certain embodiments, the energy delivery chamber containing the LPM may also comprise a diagnostic device, for example, an analyte sensor, for detecting and, optionally, quantifying analytes that may be present in the LPM. These diagnostic devices can serve as chemical sensors, biosensors, or can provide other measurements to form a complete sampling and measurement system. An element having an internal channel for fluid transfer can be fabricated together with a sensor to form a disposable unit. The device can also be adapted to include or be provided as a disposable unit that provides for collection of analytes in the LPM for analysis.

Alternatively, the diagnostic element can be located elsewhere (e.g., separate from the energy device) and the contents of the energy delivery chamber in contact with tissue can be pumped using mechanical forces, capillary forces, ultrasound, vacuum, or electroosmotic forces into a sensing chamber and analyzed.

In certain embodiments, e.g., when evaluating topical formulations or determining pharmacological parameters, the unit can be constructed to function as a closed loop drug delivery unit, including drug delivery means, analyte recovery means, sensing means to measure the analyte, and control means to provide a signal to the drug delivery means.

An example of the general operation of an energy-assisted analyte device is described here. A portable disposable unit is inserted into a portable or bench-top energy generator. The energy generator may also include circuitry for tissue resistance measurements, analyte concentration measurements, and display of analyte concentration measurements. The system (e.g., energy applicator and disposable unit) is placed against the tissue, and energy is applied for a certain period of time, either alone or as a combination with other physical, mechanical, electrical, and chemical forces. The tissue of interest is liquefied, and analytes from the liquefied tissue are collected in the disposable unit and are measured using appropriate assays for point of care diagnostics or sent to a lab for analysis.

Ultrasound Devices

Ultrasound is one form in which energy can be applied to a tissue of interest, and it can be used as a potent source of energy for sampling tissues. Any of a variety of ultrasound devices can be used or can be readily adapted for use in the methods disclosed herein. In general, any ultrasound device that can be applied to a tissue of interest to liquefy the tissue, solubilize analytes of interest, and collect such analytes is suitable for use in the methods disclosed herein. Exemplary ultrasound devices that can find use in the methods disclosed herein include those disclosed in U.S. Pat. Nos. 6,589,173; 6,620,123; 6,491,657; 6,234,990; U.S. Pat. Nos. 6,190,315; 6,041,253; 6,018,678; 5,947,921; and 5,814,599, each of which are incorporated herein by reference in their entirety.

An ultrasound device useful in the methods disclosed herein can also use focused or channeled ultrasound. Such devices can include an ultrasound delivery chamber that contains the ultrasound transducer and channeling means and is connected to an electrical signal generator and amplifier that provides the driving and controlling mechanism for the transducer. The device may include a vacuum pump and current generator.

In one embodiment, the device has an ultrasound delivery chamber having an ultrasound transducer connected to an electrical signal generator and amplifier through electrical contacts. In use, the ultrasound transducer is opposite the tissue-contacting surface of the chamber. The chamber housing can be made from any suitable material, e.g., a polymer or metal, while the interior walls can be made from a material that reflects, rather than absorbs, acoustic energy, such as Plexiglas, or other non-deforming material, such as metal. The interior walls can be shaped to define a lumen or cavity having a suitable shape, e.g., the shape of a truncated cone with a large opening adjacent the transducer and a small opening at the tissue contacting surface; or horn shaped, wherein the larger opening is towards the transducer and the smaller opening is towards the tissue contacting surface. In one exemplary embodiment, the transducer has a hemispherical shape and defines the cavity such that the rounded portion of the hemisphere is opposite the tissue contacting surface. Backing material can provide support for and insulation of the transducer.

In use, the cavity is filled with LPM. The interior surface of the walls facing the cavity may be lined with an ultrasound reflecting medium such as a metal, polymer, or ceramic material. Metals such as aluminum may be of particular use due to their high heat conductivity which may minimize temperature increase upon ultrasound application. An adhesive layer on the bottom of the chamber can be used to attach the chamber to the tissue (e.g., skin) surface.

The chamber can be optionally connected to a vacuum pump through a port which opens into the LPM. The chamber can optionally include additional means for applying force to the tissue. In one exemplary embodiment, a pair of electrodes is included for application of electric current to the tissue as an additional mechanism for liquefaction enhancement. The necessary current is provided by a generator. The chamber can also optionally include one or more diagnostic means for qualitative or quantitative analysis of sampled analytes.

In another exemplary embodiment, the device includes a chamber and an ultrasound probe. The chamber may have a variety of shapes as described above (e.g., cylindrical with open ends). One open end of the chamber is placed against the tissue at the desired location. Where desired, a hydration solution (e.g., saline) is placed in the chamber for a period of time from above zero minutes to about one hour in order to hydrate the skin. The hydration solution can then be replaced with liquefaction promoting medium, as described below in more detail. The liquefaction promoting medium can optionally include one or more surfactants, abrasive particles, protease inhibitors, RNase inhibitors, or DNase inhibitors. Following application of ultrasound and liquefaction of tissue constituents, the solution can be withdrawn from the chamber, e.g., by application of vacuum, and the solution can then be assayed.

The Ultrasound Transducer

The ultrasound transducer is used to control the parameters of the ultrasound energy applied through the ultrasound device. The ultrasound transducer may be, for example, a piezo, ceramic, or polymer block. The transducer may be operated at an appropriate frequency, e.g., in the range of between 20 kHz and 20 MHz using appropriate electrical signal generators and amplifiers. The transducer preferably is operated at a frequency in the range of between 20 kHz and 1 MHz. Other ultrasound parameters including, but are not limited to, intensity, amplitude, duty cycle, fluence, mechanical index, thermal index, distance from the tissue, and application time may be varied to achieve sufficient liquefaction of the tissue and solubilization of analytes of interest.

The intensity of ultrasound can be chosen so as to keep the exposed tissue functionally unaffected. A typical intensity used for this purpose is in the range of 1-10 W/cm$^2$. The range of energy fluence for this application is between 1-6000 J/cm$^2$. Higher intensities will produce a greater degree of liquefaction. The duty cycle can vary from between one and 100%. The transducer can be positioned at a distance from the tissue between 0.5 and 10 mm. The application time can range between 1 seconds and 10 minutes. In some embodiments, ultrasound is applied to the tissue for greater than 1 minute, at least 90 seconds, or at least 2 minutes or more in order to produce a suitable liquefied tissue sample. Longer exposure times will yield a higher amount of tissue liquefaction.

Excessively high ultrasound energy and exposure times may lead to significant adverse effects on the tissue or its constituents. One particularly evident adverse effect is elevation of tissue temperature, also known as the thermal effect of ultrasound. Other adverse effects include redness and bleeding. To facilitate tissue liquefaction while mitigating unacceptable adverse side effects of exposed tissue or its constituents, the degree of liquefaction can be monitored and ultrasound parameters controlled for individual subjects. This may be achieved by measuring a feedback parameter before, during or after application of energy. "Feedback parameter" as used herein refers to a parameter of the energy applied and/or the status of the tissue liquefaction, where such parameters may be assessed directly (e.g., by monitoring time of application to tissue) or indirectly (e.g., by monitoring a change in LPM, such as temperature, change in protein content (or other tissue constituent), and the like). Feedback parameters can be measured qualitatively or quantitatively. Exemplary feedback parameters to be measured may include, but is not limited to, mechanical (for example, Young's modulus), thermal (for example, temperature), optical (for example, reflectance), and electrical (for example, resistance) properties of the tissue. Further exemplary feedback parameters include optical (for example, turbidity (e.g., as assessed by light scattering), chemical (for example, pH, qualitative or quantitative concentration of a selected constituent (e.g., calibrator analyte)), thermal (for example, temperature) or electrical (for example, electrical resistance) properties of LPM. For example, an increase in temperature of the LPM to greater than 50° C. indicates likelihood of tissue damage.

In an exemplary embodiment, energy is applied to a site, the feedback parameter is continuously measured, and application of energy is terminated when the parameter reaches a threshold value, which may be correlated with a safety limit for exposure of the subject tissue to the energy being applied. When the feedback parameter exceeds a threshold value, energy application can be decreased in intensity or can be terminated to avoid undesirable damage to the tissue and/or the tissue constituents that may be present in the LPM. Examples of such measurement include but are not limited to measurements of temperature, optical absorbance, pH, or electrical conductivity of LPM. Application of energy increases the temperature of LPM. Whereas human tissues can tolerate increased temperature for short periods of time, it is desired to limit the elevation of temperature and duration of hyperthermia.

In one embodiment, the energy application device is accompanied by a thermocouple to measure temperature of LPM during energy application to the tissue. The device will turn off when the temperature reaches a threshold value. This threshold value will vary depending on the tissue and the thermal properties of LPM, and is between 36 and 70° C. In yet another embodiment, the device can measure optical absorbance of LPM. Liquefaction of tissues increases the turbidity of LPM and hence optical absorbance and scattering. Continuous measurement of optical absorbance or scattering accompanied by automatic shut-off upon reaching a threshold can be used to control liquefaction. This feature of continuous monitoring of tissue liquefaction can be used in conjunction with any type of energy source.

In some embodiments, the thermal properties (e.g., temperature, heat-capacity, and the like) of the LPM can be manipulated before or during ultrasound liquefaction so as to reduce the adverse thermal effects of ultrasound exposure on tissue or its constituents. In one embodiment, a pre-cooled LPM having temperature lower than the ambient temperature can be used for ultrasound liquefaction. In another exemplary embodiment, the temperature of the LPM can be continuously reduced during ultrasound exposure by transferring its heat to a pre-cooled liquid flowing through a heat-transfer jacket coupled to the LPM-containing reservoir. This feature of manipulating the thermal properties of LPM to avoid adverse thermal effects of energy exposure can be used in conjunction with any type of energy source. In another embodiment, LPM can be continuously circulated through the device so as to minimize elevation of LPM temperature prior to collection for analysis.

It is also expected that the device can be moved around to expose a large area of the tissue to ultrasound. Exposure to large areas increases the amount of tissue liquefied.

Focused ultrasound may also be achieved by using a phased array of transducers, which can be composed of, for example, multiple individual transducers arranged to form a hemispherical wall. Each transducer of the phased array can be individually activated using signal generators and amplifiers.

Although it may be less desired, the transducer can be implanted in the body, brought into proximity of a tissue of interest, or contacted directly to a tissue of interest.

Abrasive Devices

In certain embodiments, abrasive force can be generated by setting an abrasive surface in motion, with the abrasive surface held in contact with a tissue of interest. For this purpose a mechanized device that bears the abrasive surface and is capable of setting the surface into motion can be introduced into a chamber containing LPM. Such a chamber, when placed in contact with the tissue, can expose the tissue to the mechanized abrasion device such that the abrasive surface of the device can be held in contact with the tissue. Setting the abrasive surface in motion (e.g., by rotating, or a similar periodic oscillatory movement) can dislodge the tissue constituents and collect them directly into the LPM.

Non-limiting examples of abrasive surface can be a disc made of abrasive material (e.g., fabric, polymer, abrasive crystals (e.g., quartz, metal, silica, silicon carbide, dust and derivatives of aluminum (such as $AlO_2$), diamond dust, and the like), etc.); a disc bearing sanding paper with its abrasive side designed to face the tissue of interest; and a brushing device bearing bristles which form the means for abrading tissues. The contact area of the abrasive surface may be chosen to be up to 10 $cm^2$; however, larger contact area may be warranted depending on the quantity of analytes to be sampled and/or the area of the tissue to be inspected. The pressure applied by the abrasive surface onto the tissue may be varied in the range of 1-2000 $N/m^2$. Higher pressures may also be applied to the tissue, but such an application would require careful control of the applicator device. A preferred range of pressure is about 100 to about 1000 $N/m^2$. The duration of contact time between the tissue and the surface may range from 1 second to 60 minutes; however, application time may be more depending on the tissue type, the amount of tissue constituent, and the area of tissue to be sampled.

In exemplary embodiments of devices with sanding paper, the sanding paper may be coated with abrasive crystals (e.g., silicon carbide, aluminum oxide, and the like), where the grit sizes can be of any appropriate size, e.g., from about 40 up to 2000.

In exemplary embodiments of brushing devices, the stiffness of the bristles may be varied, as measured by the Robertson number ranging from about 1 to about 15 is preferred. The length of the bristle may be varied from about 0.5 mm to about 20 mm. The contact angle of the bristle with the tissue may also be varied between 0°-90°. Additionally, the bristles might be made of natural or synthetic material, non-limited to animal fibers, metal, and polymers (such as polyamides, and the like). Bristles having edges with different shapes including but not limited to spherically-round, flat, and V-shaped (pointed) may be devised for abrasive sampling.

In an exemplary embodiment, the chamber containing the LPM can be optionally connected to a vacuum pump through a port which opens into the LPM. The chamber can optionally include additional means for applying force to the tissue. In one exemplary embodiment, a pair of electrodes is provided for application of electric current to the tissue as an additional mechanism for extraction enhancement. The current is provided by a generator. The chamber can also optionally include one or more diagnostic means for qualitative or quantitative analysis of sampled analytes.

Absorbent abrasive devices essentially comprise an abrasive surface made of hard materials, such as silica, diamond, or metals, which can apply abrasive force to a tissue as described above, and can retain the dislodged tissue constituents. These devices can abrade the tissue due to the rotational, translational, or oscillatory motion of the abrasive surface on the tissue such that the abraded tissue and its constituents are collected in an absorbent pad comprising a biocompatible material that holds liquefaction promoting medium and the resultant liquefied tissue. In an exemplary embodiment, the absorbent pad can be made of absorbent fabric with interwoven/embedded abrasive entities, and the like. The LPM can be separated from the absorbent pad to produce a liquefied tissue sample that can be analytically processed for the presence or absence of one or more tissue analytes of interest.

Abrasive force can be applied to tissues by means of a mechanized liquid stirrer. In such a device, LPM containing abrasive particles, surfactants, or other liquefaction promoting agents is placed in contact with the tissue and abrasive force is applied by stirring the LPM. The stirring motion can be achieved by placing a liquid stirrer in the LPM and accomplishing a rotation rate of up to 50000 rpm of the LPM. Higher stirring rates may be warranted depending on the tissue type and amount of the tissue constituents needed to be sampled. Exemplary stirring devices that can find use in the methods disclosed herein include those disclosed in U.S. Pat. No. 4,169,681, U.S. Pat. No. 7,278,781, and U.S. Pat. No. 7,364,351 each of which are incorporated herein by reference in their entirety. The LPM can be analyzed for the presence or absence of one or more tissue analytes.

Devices for abrasion by a high velocity jet comprise a stream of fluid that moves at high velocity and comprises abrasive particles such as silica, silicon carbide, $AlO_2$, and the like, which impact the tissue and abrade it. Abraded tissue can be collected in liquefaction promoting media to generate liquefied tissue sample. The liquefied tissue sample can be analytically processed for the presence or absence of one or more tissue analytes.

In a typical embodiment, such a device would employ a pressurized fluid generator, comprising a compressor, that conveniently generates a compressed gaseous jet of, for example, air or a non-reactive gas; an abrasive substance supply means, which supplies abrasive substances (e.g., microcrystals of quartz, metal, silica, silicon carbide, dust and derivatives of aluminum (such as $AlO_2$), diamond dust, and the like) to the gaseous jet; and a means that applies the gaseous jet containing the abrasive substance to the tissue of interest as well as redirects the jet to a collection reservoir for collecting the dislodged tissue constituents from the jet. The gaseous jet may be applied to the tissue of interest such that the jet stream's contact angle with the tissue is between 0°-90°, which may be chosen to facilitate the jet's redirection to the collection reservoir.

In one embodiment, the said collection reservoir may contain the liquefaction promoting medium for collecting and liquefying the abraded tissue constituents from the said gaseous jet. Abrasion devices employing such an abrasion method may additionally comprise a suction means for facilitating the flow and exit of the jet through the collection reservoir. Exemplary abrasion devices that can find use in the methods disclosed herein include those disclosed in U.S. Pat. No. 5,207,234, U.S. Pat. No. 5,037,432, U.S. Pat. No. 6,238,275, U.S. Pat. No. 6,277,128, U.S. Pat. No. 6,277,128, U.S. Pat. No. 5,810,842, and U.S. Pat. No. 6,039,745, each of which are incorporated herein by reference in their entirety.

In the process, the tissue constituents dissolve into the LPM. The LPM can be analyzed for the presence or absence of one or more tissue analytes. As with the ultrasound embodiments described above, feedback parameters can be monitored before, during and after application of energy.

Liquefaction-Promoting Medium (LPM)

The LPM can be designed to serve three purposes: a) it facilitates dispersion of tissues into its constituents, b) it acts as a medium to collect liquefied tissue constituents, and c) it inhibits degradation of the sampled constituents such that their chemical or biological activity is retained (e.g., by preserving various molecules' structural conformation and by preserving the ability of sampled microbes to multiply).

In general, LPM comprises a hydrophilic solvent, such as aqueous solutions (e.g., phosphate buffered saline, etc) or organic ("non-aqueous") liquids (e.g., DMSO, ethanol, and the like), which may additionally contain a variety of liquefaction-promoting agents, including but not limited to surfactants (non-ionic, anionic, or cationic), fatty acids (e.g., both saturated and unsaturated fatty acids, (e.g., Hexanoic acid, Octanoic acid, Decanoic acid, Dodecanoic acid, Palmitic acid, Stearic acid, Oleic acid, Linoleic acid, Linolenic acid, Cholic acid.)), azone and azone-like compounds (e.g., n-lauryl caprolactam, laurocapram, tranzone, Methyl pyrrolidone, Cyclohexyl pyrrolidone, Octyl pyrrolidone, Decyl pyrrolidone, Decyl methylpyrrolidone, Methyl piperazine, Phenyl piperazine, Octanamide, Hexadecanamide, Caprolactam), chelating agents (e.g., EDTA, etc), inorganic compounds, and abrasive particles. "Liquefaction-promoting agent" as used herein refers to a component of a LPM which can facilitate liquefaction of a tissue sample and/or solubilization of tissue constituents. Depending on the tissue type and the analytes of interest, constituents of the LPM can be rationally selected based on the criteria described above. For example, a delicate tissue, such as mucosal membrane, can be liquefied by a saline solution with minimal or no surfactants, whereas keratinized tissues, such as skin, will require additional constituents, such as surfactants. The LPM can be formulated to meet the needs of a particular application. Example formulations include but are not limited to liquids or semi-solid compositions. Exemplary compositions include gels, creams, and pastes.

The agents within the LPM can comprise a variety of suitable components including, but not limited to: water, saline, alcohols (including ethanol and isopropanol (e.g., in a concentration range of 10-100% in aqueous solution)), abrasive particles, such as silica, aluminum oxide, or silicon carbide (e.g., in a concentration range of 0.01-99% (w/v) in water-based solution), surfactants, such as Brij (various chain lengths, e.g., Brij-30), N-lauroyl sarcosine (NLS), Triton X-100, Sodium Dodecyl Sulfate (SDS) and Sodium Lauryl Sulfate (SLS), HCO-60 surfactant, Hydroxypolyethoxydodecane, Lauroyl sarcosine, Nonoxynol, Octoxynol, Phenylsulfonate, Pluronic, Polyoleates, Sodium laurate, Sodium oleate, Sorbitan dilaurate, Sorbitan dioleate, Sorbitan monolaurate, Sorbitan monooleates, Sorbitan trilaurate, Sorbitan trioleate, Span 20, Span 40, Span 85, Synperonic NP, Tweens, Sodium alkyl sulfates, and alkyl ammonium halides, (e.g., in concentrations ranging between 0.01-20% in water-based solution), DMSO (e.g., in a concentration range of between 0.01-20% in water-based solution), fatty acids such as linoleic acid (e.g., in a concentration range of between 0.1-2% in ethanol:water (50:50), azone (e.g., in a concentration range of 0.1-10% in ethanol:water (50:50), polyethylene glycol (e.g., in a concentration range of 10-50% in water-based solution), histamine (e.g., in a concentration range of 10-100 mg/ml in water-based solution), EDTA (e.g., in a concentration range of 1-100 mM), and sodium hydroxide (e.g., in a concentration range of 1-100 mM). In some embodiments the LPM may contain surfactants other than TWEEN, CTAB, SPAN, or Sodium Alkyl Sulfate. In some embodiments, the LPM may contain surfactants other than cationic surfactants. Where the LPM includes a surfactant, the total concentration of the surfactant (w/v) in the LPM can range from at least 0.5%, to 10%, and can be, for example, about 0.5%, about 1%, about 1.5%, about 2%, about 2.5%, or about 3%.

The LPM can include agents that facilitate preservation of bioactivity of an analyte of interest. For example, the LPM can contain free radical scavengers (e.g., antioxidants (e.g., polyphenol, beta-carotene, lutein, lycopene, selenium, etc), vitamin A, vitamin C, vitamin E, alpha-tocopherol, butylated hydroxytoluene, sodium benzoate, sodium formate, and the like); defoaming agents (e.g., silicone or non-silicone anti-foaming agents such as dimethylpolysiloxane, hydrocarbon oil, low fatty acid diglyceride, and the like); and shear protectants (e.g., polyethylene glycol, polyvinyl alcohol, pluronic F68, and the like). "Bioactivity" as used in the context of an analyte refers to a structural conformation that facilitates detection (e.g., such as an epitope bound by a specific antibody or other structural feature that is sensitive to denaturation), and may also include a biological activity of an analyte. (e.g., enzymatic activity).

LPM of particular interest are those that contain a combination of surfactants that when used in connection with the methods disclosed herein provides for a desired level of tissue constituents in the LPM while providing for preservation of bioactivity of analytes in the LPM, particularly so as to provide for maintenance of structural conformation of an analyte(s) (e.g., avoid denaturation of a protein analyte).

As set out in the Examples below, use of different combinations of surfactants for sampling skin revealed that a combination of nonionic surfactant and anionic surfactant in the LPM provided for both high levels of tissue constituents in the LPM and good preservation of bioactivity of an analyte contained in the LPM following use in a method described herein.

Non-limiting examples of nonionic surfactants of interest include Triton X surfactants, Sorbitan surfactants, and Brij series surfactants. Exemplary Triton X surfactants include Triton X-15, Triton X-45, Triton X-100, Triton X-114, Triton X-165, Triton X-200, Triton X-207, Triton X-305, Triton X-405, and the like. Exemplary Sorbitan surfactants include Span-20, Span-40, Span-60, Span-65, Span-80, Span-85, and the like. Brij series surfactants are generally characterized by R—(—O—$CH_2$—$CH_2$—)$_n$—OH, wherein n is an integer, usually from at least 2 or more and can be 100 or more, and "R" is a saturated or unsaturated, branched or linear, hydrocarbon chain (e.g., a saturated or unsaturated, branched or linear, $C_5$-$C_{30}$, $C_8$-$C_{20}$, or $C_{10}$-$C_{18}$ alkyl chain). Exemplary Brij series surfactants of interest include Polyethylene glycol dodecyl ether (Brij 30), Polyoxyethylene 23-lauryl ether (Brij 35), Polyoxyethylene 2-cetyl ether (Brij 52), Polyoxyethylene 10-cetyl ether (Brij 56), Polyoxyethylene 20-cetyl ether (Brij 58), Polyoxyethylene 2-stearyl ether (Brij 72), Polyoxyethylene 10-stearyl ether (Brij 76), Polyoxyethylene 20-stearyl ether (Brij 78), Polyoxyethylene 2-oleyl ether (Brij 92), Polyoxyethylene 10-oleyl ether (Brij 96), Polyoxyethylene 100-stearyl ether (Brij 700), Polyoxyethylene 21-stearyl ether (Brij 721)). Of particular interest are the Brij series surfactants Brij 30, Brij 35, and Brij 52.

Non-limiting examples of anionic surfactants of interest include acyl sarcosines, or salts thereof, particularly alkali metal salts, such as sodium. Of particular interest are N-lauroyl sarcosine, Sodium Cocoyl Sarcosinate, Sodium Myristoyl Sarcosinate, Isopropyl Lauroylsarcosinate, Sodium Palmitoyl Sarcosinate, and Disodium Lauroamphodiacetate Lauroyl Sarcosinate. As used herein, the term "anionic surfactant" refers to anionic surfactants and salts thereof.

The term "sarcosine surfactant" refers to any surfactant comprising an acyl sarcosine compound or salt thereof.

The ratio of non-ionic surfactant to anionic surfactant present in the LPM can be adjusted to achieve desired results. Non-limiting ratios of interest include 10:90 non-ionic:anionic, 25:75 non-ionic:anionic surfactant, 50:50 non-ionic:anionic surfactant, 75:25 non-ionic:anionic surfactant, and 90:10 non-ionic:anionic surfactant. A mixture of particular interest is a 50:50 surfactant mixture of a Brij series surfactant (e.g., Brij-30) and N-lauroyl sarcosine (NLS). As illustrated in the Examples below, this combination of surfactants, when included in the LPM at a total surfactant concentration of 1% (w/v), provided for solubilization of a high level of tissue constituents as assessed by total protein concentration, and provided for retention of bioactivity (as assessed by ELISA technique).

In some specific cases, for example, the collection of live pathogens, different LPM compositions can be used to achieve desired results. Saline was used as an LPM to provide for collection of a wide variety of skin-resident bacteria, and additionally, these microbes remained potent to multiply and grow ex vivo. It will be evident to the ordinarily skilled artisan upon reading the present disclosure that LPM compositions varying in components can be readily produced for use in specific applications.

LPM can also include stabilizers of analytes of interest, such as protease-inhibitors, RNase-inhibitors, and DNase-inhibitors, which can provide for collection and at least temporary storage of analytes with minimal or no detectable degradation or loss of bioactivity. Other exemplary liquefaction-promoting agents are described in U.S. Pat. No. 5,947,921, which is incorporated herein by reference in its entirety. For example, the liquefaction-promoting agent can include surfactants, abrasive particles, and biomolecule stabilizers.

In one exemplary embodiment, the LPM is composed of a solution of 1% w/v mixture of NLS and Brij-30 in sterile PBS. In certain embodiments, specifically where the analytes are one or more proteins, the LPM contains a 1-10% v/v protease inhibitor cocktail (e.g., catalog number: P8340, provided by Sigma-Aldrich, St. Louis, Mo.). In certain embodiments, the LPM is a saline solution.

In some embodiments, the thermal properties (e.g., temperature, heat-capacity, and the like) of the LPM can be manipulated before or during tissue liquefaction so as to reduce the adverse thermal effects of energy exposure on tissue and/or its constituents. In an exemplary embodiment, a pre-cooled LPM having temperature lower than the ambient temperature (about 25° C.) can be used for ultrasound liquefaction. In another exemplary embodiment, the temperature of the LPM can be continuously reduced during energy exposure by transferring its heat to a pre-cooled liquid flowing through a heat-transfer jacket coupled to the LPM-containing reservoir.

Analytes

A variety of analytes can be detected (qualitatively or quantitatively) according to the methods disclosed herein and, optionally, characterized to provide an analyte profile of the tissue in question. Non-limiting examples include: structural and signaling proteins (e.g., keratins (e.g., basic keratins, acidic keratins), β-actin, interleukins, chemokines, growth factors, colony-stimulating factors, interferons, antibodies (IgE, IgG, IgA, IgD, IgM), cancer biomarkers (e.g., CEA, and the like), heat shock proteins (e.g., Hsp-60, Hsp-70, Hsp-90, etc.), and the like), lipids (e.g., cholesterol, ceramides (e.g., ceramides 1-6), fatty acids, triglycerides, paraffin hydrocarbons, squalene, cholesteryl esters, cholesteryl diesters, free fatty acids, lanosterol, cholesterol, polar lipids (e.g., glucosyl-derivatives and phospholipids), and the like), nucleic acids (e.g., RNA and DNA), small molecules (e.g., free amino acids, lactate, exogenously delivered drug molecules, environmental contaminants, warfare agents, and the like) and microorganisms (e.g. bacteria, fungi, viruses and the like). These analytes are found within the tissue itself, and may not be solely present in the interstitial fluid around the tissue. The analyte may be other than a marker associated with interstitial fluid, such as a tumor marker. Thus, the methods disclosed herein can be adapted to detect tumor markers that are present in tissue structures, but which may or may not also be present in interstitial fluid.

In a particular embodiment, antibodies against allergens and cytokines are liquefied and characterized to provide an allergy profile for the tissue and the subject in question. Specific types of antibodies include but are not limited to IgE and IgG antibodies. Specific types of cytokines include but are not limited to IL4, IL5, IL10, IL-12, IL13, IL-16, GM-CSF, RANTES, MCP-4, CTACK/CCL27, IFN-g, TNFa, CD23, CD-40, Eotaxin-2, and TARC.

The analytes can be analyzed in many ways, which can be readily selected by the ordinarily skilled artisan in accordance with the analyte to be evaluated. A reservoir or collecting container can be applied to the site for collection of sample, which is then measured using analytical techniques. Application of energy can be optimized to maximize analyte recovery. It may be desirable for certain applications to maintain the relative levels of the analyte to other components of the sample. Exemplary assay methods include but are not limited to gel electrophoresis, agar plating, enzymatic testing, antibody-based tests (e.g., western blot tests, Enzyme-Linked Immuno Sorbent Assay (ELISA), lateral flow assay, and the like), thin layer chromatography, HPLC, mass spectrometry, radiation-based tests, DNA/RNA electrophoresis, (UV/Vis) spectrophotometry, flow assays, and the like.

A quantitative measurement of the presence of tissue constituents in the liquefied tissue sample can assess the extent of tissue liquefaction. Such an internal calibration can be accomplished by measuring one or more optical properties of the liquefied tissue sample such as absorbance, transmittance, scattering, or fluorescence emission upon being irradiated by a source emitting electromagnetic waves. Additional sample parameters such as gravimetric-weight, total protein content, pH, and electrical conductance can be used for calibrating the extent of liquefaction. Further, measurement of tissue properties such as thickness, rate of water loss, and electrical conductivity can be used. Direct measurement of the concentration of one or more sampled analytes such as β-actin, β-tubulin, GAPDH (glyceraldehyde 3-phosphate dehydrogenase), LDH (lactate dehydrogenase), or any other abundantly-present biomolecule whose concentration is expected to remain constant in the tissue, can be used for calibrating the extent of tissue liquefaction.

Tissue Cells and Microorganisms

In addition to the analytes described above, whole cells of tissue under analysis, as well as a variety of microorganisms, can be detected in tissues of interest using the methods disclosed herein. Tissue cells and most microorganisms are much larger than the analytes described above, and their extraction from a tissue of interest can be accomplished using various embodiments disclosed herein. Pathogenic bacteria, virus, protozoa, and fungi play well-known roles in various infectious diseases, and their detection can facilitate a diagnosis of a disease caused by the microorganism (e.g., tuberculosis, herpes, malaria, ringworm, etc.). When a subject is suspected of having an infection with such a microorganism, the methods disclosed herein can be used to detect the presence or absence of a microorganism, and facilitate diagnosis of the condition.

Non-pathogenic microorganisms are normally present in healthy tissues ("normal flora"), and can play a role in many bodily functions and maintenance of health of a subject. Detection of these normal flora microorganisms (e.g., bacteria) in a tissue of interest can also be accomplished using the current method. A subject's tissue can be sampled and analyzed using the methods disclosed herein to examine the various microorganisms that are naturally present. When a subject is suspected to have an abnormal condition, tissue of the subject can be sampled according to the methods disclosed herein to detect the presence or absence of a change in a profile of non-pathogenic microorganisms relative to that of a normal, healthy subject. A change in this microorganism profile can facilitate diagnosis of a condition of interest in the subject.

In some embodiments, tissues can be liquefied to recover their cells or microorganisms residing therein. As exemplified in Example 4 below, application of the present methods using energy provide for collection of bacteria from skin of a subject into a collection medium which may optionally contain an LPA. For example, application of ultrasound energy to the tissue of interest using PBS was sufficient to collect bacterial microflora. In general, practice of this method involves application of a sufficient level of ultrasound energy so as to dislodge microorganisms from the tissue and enter the collection medium, which is then collected for subsequent analysis, which may include culturing the medium to determine whether certain microorganisms are present, directly assaying the medium (e.g., using ELISA techniques (e.g., involving microorganism-specific antibodies), genomics analysis, microscopy), or a combination of these approaches. Detection of microorganisms in the medium facilitates diagnosis of a condition of interest.

The methods described herein can also be used to collect cells from the tissue. Application of energy with an appropriate LPM that liquefies tissues without disrupting cell membranes can be used to harvest whole cells, including viable whole cells from tissues. LPM in this case may comprise chemicals including but not limited to ion chelating agents such as EDTA, antibiotics to decrease risk of contamination, or enzymes such as trypsin to dislodge the cells. Similarly, with changes in parameters of energy and/or LPM as discuss above, the methods of the present disclosure can be used to collect nuclei or other cellular organelles.

Tissues of Interest

A variety of tissues are well suited to the methods and compositions of the present disclosure, and may be present in or obtained from a variety of different subjects. The term "subject," as used herein, refers to any mammalian or non-mammalian animal, including but not limited to humans, lab animals, research animals, livestock, pets, and wild animals; reptiles; avian species; and amphibians. Humans are of particular interest. Tissue from a subject may be live, dead, freshly collected, frozen, or preserved.

Exemplary tissues of interest include but are not limited to skin, mucosal membranes (nasal, gut, colon, buccal, vagina etc.) or mucus, breast, prostate, eye, intestine, bladder, stomach, esophagus, nail, testicles, hair, lung, brain, pancreas, liver, heart, bone, or aorta wall. In one embodiment, the tissue is skin, which can be skin of the face, arms, hands, legs, back, or any other location. While skin and mucosal surfaces are highly accessible for performing liquefaction, devices pertaining to liquefaction methods described in this disclosure can be designed to readily adapt to various internal tissues listed above. Exemplary devices specific to internal tissues that can find use in the methods disclosed herein include those disclosed in U.S. Pat. No. 5,704,361, U.S. Pat. No. 5,713,363, and U.S. Pat. No. 5,895,397, each of which are incorporated herein by reference in their entirety.

In some embodiments, the tissue of interest is other than a tumor or a tissue suspected of being a tumor. Where the methods disclosed herein are applied to detection of a microorganism, the tissue of interest is one suspected of containing a microorganism (e.g., a tissue suspected of having an infection, particularly a deep tissue infection, e.g., infection of the dermal and/or subdermal layers of the skin, including such layers of mucosal membranes).

Methods of Use

The methods disclosed herein can be used for a broad range of tissue evaluations, including assessment of the presence or absence of an analyte(s) of interest to facilitate diagnosis of a condition of interest. In some embodiments, the methods find use where, for example, the patient presents with clinical signs and symptoms suggestive of one or more conditions, where the methods disclosed herein can facilitate a differential diagnosis.

In certain embodiments, the present disclosure provides methods that involve comparing a test analyte profile generated from a patient sample to a reference analyte profile. A "reference analyte profile" or "analyte profile for a reference tissue" generally refers to qualitative or quantitative levels of a selected analyte or set of 1, 2, 3, 4, 5, 6, 7, 8, 9, 10 or more analytes, which are characteristic of a condition of interest. Exemplary conditions of interest for which a reference analyte profile may be provided include, but are not limited to, normal reference analyte profile (e.g., healthy tissue (i.e., absence of disease), general tissue health, acceptable or tolerated levels of an analyte (e.g., a drug, environmental contaminant, etc.), disease reference analyte profile (e.g., an analyte profile characteristic of the presence of, for example, microbial infection (e.g., bacterial, viral, fungal, or other microbial infection), localized diseases in tissues (e.g., dermatitis, psoriasis, cancers (prostate, breast, lung, etc.), urticaria, etc.), systemic diseases manifested in tissues (e.g., allergies, diabetes, Alzheimer's disease, cardio-vascular diseases, and the like); etc.), environmental contaminant reference analyte profile (e.g., an analyte profile characteristic of the presence of unacceptably high levels of an environmental contaminant (e.g., warfare agent, pollens, particulates, pesticides, etc.), drug reference analyte profile (e.g. an analyte profile characteristic of therapeutic levels of a drug, drug-of-abuse (e.g., to facilitate assessment of drug-of-abuse), etc.); and the like. Reference analyte profiles may include analytes that are members of one or more classes of analytes (e.g., proteins (e.g., antibodies, cancer biomarkers, cytokines, cytoskeletal/cytoplasmic/extra-cellular proteins, and the like), nucleic acids (DNA, RNA), lipids (which include ceramides, cholesterol, phospholipids, etc.), biologically-derived small molecules, drugs (e.g., therapeutic drugs, drugs-of-abuse), environmental contaminants, warfare agents, etc.) or members of a subclass of analytes (e.g., antibodies, phospholipids). Reference analyte profiles of a given condition of interest may be previously known in the art or may be derived from the tissue using the methods described in the present disclosure. Reference analyte profiles can be stored in electronic form (e.g., in a database) to provide for ready comparison to a test analyte profile to facilitate analysis and diagnosis.

A "test analyte profile" or "analyte profile for a tissue of interest" refers to qualitative or quantitative levels of a selected analyte or set of 1, 2, 3, 4, 5, 6, 7, 8, 9, 10 or more analytes, to facilitate diagnosis or prognosis of a condition of interest. A test analyte profile may include analytes that are members of one or more classes of analytes (e.g., proteins, nucleic acids, lipids, biologically-derived small molecules, drugs (e.g., proteins (e.g., antibodies, cancer biomarkers, cytokines, cytoskeletal/cytoplasmic/extra-cellular proteins, and the like), nucleic acids (DNA, RNA), lipids (which include ceramides, cholesterol, phospholipids, etc.), biologically-derived small molecules, drugs (e.g., therapeutic drugs, drugs of abuse), environmental contaminants, warfare agents, etc.) or members of a subclass of analytes (e.g., antibodies, phospholipids). In general, the analytes selected for analysis to generate a test analyte profile are selected according to analytes of a desired reference analyte profile. Comparison of a test analyte profile to an appropriate reference analyte profile facilitates determining the presence or absence of the condition or state of interest, e.g., by assessing whether there is a substantial "match" between a test analyte profile and a reference analyte profile.

Methods for generating reference and test analyte profiles of a selected analyte or set of analytes can be accomplished using methods available in the art, and will be selected according to the analyte(s) to be assessed.

The current methods can be used for a broad range of tissue evaluations. Energy-assisted tissue liquefaction can provide a quantitative evaluation and profile of normal tissue. Comparison of the normal tissue profile with a profile of tissue under investigation can facilitate diagnosis of changes in tissue microenvironment (e.g. up/down-regulation of several proteins, lipids, nucleic acids, small molecules, drugs, etc) which can indicate various diseased conditions such as allergies, cardio-vascular disease, dermatitis, etc. The methods can also be used as a tool for monitoring tissue recovery and evaluating therapeutic efficacy of various treatments (as in monitoring of therapy, which can be combined with modification of therapy as desired or needed). The analyte profiling methods can also provide tools for the personal-care industry for evaluation of topical formulations (e.g., as in cosmetics). This methodology can be utilized for determining pharmacologic parameters by liquefying tissues and detecting the drug molecules therein. In a similar manner, rapid and routine testing of chemicals, bio-hazardous contaminants, and drugs-of-abuse can also be quantitatively accomplished. The methods can also be used for sensitive detection and diagnosis of pathogenic microflora.

In certain embodiments, the current methods provide a profile of normal tissue, wherein normal tissue is defined by the absence of the abnormal tissue condition of interest. Energy is applied to the normal tissue, e.g., by ultrasound exposure or abrasion, in the presence of a liquefaction-promoting agent. Various tests are performed upon the liquefied tissue sample to isolate and identify the analytes present in the tissue.

In certain embodiments, the methods can be applied to facilitate diagnosis of various tissue diseases which are characterized by a quantitative evaluation of a change in the tissue microenvironment. This evaluation is performed by comparing an analyte profile of a reference tissue (e.g., a reference analyte profile, which may be stored in a database) with the analyte profile of the tissue of interest (i.e., the test analyte profile). The quantitative presence or absence of a certain analyte or set of analytes present in a tissue under investigation, when compared to the quantitative presence or absence of the same analytes in a reference tissue will indicate the presence or absence of a particular disease, and thus facilitate diagnosis of the condition. The reference analyte profile can be one characteristic of tissue which is known to not be affected with the disease in question, or can be a reference analyte profile characteristic of the disease in question for the tissue in question.

In one embodiment, the tissue under investigation is skin and/or mucosal membranes, and the quantitative test analyte profile is compared to a reference analyte profile to determine the presence or absence of a disease such as allergy, urticaria, microbial infection, auto-immune disease, cardio-vascular disease, or cancer.

In certain embodiments, this method can be used to monitor tissue recovery. This monitoring is performed by comparing an analyte profile of reference tissue with the analyte profile of tissue under investigation. The quantitative presence or absence of a certain analyte or composition of analytes present in a tissue under investigation, when compared to the quantitative presence or absence of the same analytes in a reference tissue can indicate whether or not the tissue is returning to its healthy state. The reference tissue is usually tissue that is in a healthy state.

In certain embodiments, the current methods can be used to evaluate the therapeutic effect of various treatments, including bioavailability of therapeutics in tissues of interest. The analyte in the liquefied tissue sample can be quantified to indicate how much of the analyte is present in the tissue. The quantitative presence or absence of a certain analyte or composition of analytes present in a tissue under investigation, when compared to the quantitative presence or absence of the same analytes in a reference tissue, can indicate whether or not the dosed therapeutic agent is staying in the specific tissue or body long enough to achieve its desired effect. The reference tissue is usually tissue that is in a healthy state.

In certain embodiments, the methods disclosed herein can be used to evaluate therapeutic formulations on a tissue such as skin, specifically, whether component(s) of a formulation (e.g., lotions, creams, salves, and the like) are being absorbed by the tissue, and if the amount delivered is therapeutically effective. In certain embodiments, the methods disclosed herein can include a closed loop system, in which the same system can apply the therapeutic formulation, liquefy the analytes, analyze the analyte profile, and adjust the delivery of the formulation accordingly. The reference tissue in this case would be healthy tissue, or tissue at various levels of recovery from the condition that the therapeutic formulation was treating.

In certain embodiments, the current methods can be used to determine the analyte profile for use in determining pharmacological parameters or efficacy of pharmaceutical agents. The presence or absence of certain analytes (e.g., immune system responders, cytokines) can be used to correlate certain dosages of pharmaceutical agents to biological parameters, including but not limited to bioavailability, AUC, clearance, and half life.

In certain embodiments, the methods disclosed herein can be used to detect the presence or absence of certain chemicals, including but not limited to bio-hazardous contaminants, warfare agents, illicit drugs, known pharmaceutical agents, and the like. Such methods find use in, for example, law enforcement, regulation of doping in competitive sports, evaluation of exposure and/or risk of disease as a result of exposure to toxins or contaminants, and the like.

In certain embodiments, the current methods can be used for detecting or diagnosing pathogenic microbes (e.g., bacteria, fungi, viruses, and the like). Current methodologies for microbial diagnostics in tissues, such as replica plating, swabbing, and washing, are unattractive due to large variability and low dispersion of extracts, which leads to decreased sensitivity and high protocol-dependency. Various tests can be performed upon the liquefied tissue sample to isolate and identify the microbial analytes present in the tissue. In certain embodiments, these tests include plating on agar plates.

Computer-Based Methods and Systems

The methods involving comparison of a test analyte profile to a reference analyte profile can be conducted manually, or in a variety of computer-related embodiments. For example, the comparison steps of the methods can be conducted by execution of a computer program for analyzing and comparing a test analyte profile with one or more reference analyte profiles, which reference analyte profiles may be stored in a computer database. Following the comparison, the computer can generate an output indicating the best match, or lack of a match, between the test analyte profile and reference analyte profiles in the database. In some embodiments, the results can be output in order from best match to worst match of all or a selected number (e.g., 2, 3, 4, 5, or more) of reference analyte profiles in the database.

The methods and systems described herein can be implemented in numerous ways. In one embodiment, the methods involve use of a communications infrastructure, such as the internet. Several embodiments are discussed below. It is also to be understood that the methods disclosed herein may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example: the user-side computing environment can be programmed to provide for defined test codes to denote analytes to be considered and, where desired, the reference analyte profiles against which the test analyte profile is to be compared. Following communication to the server and execution of the comparison program, the response is transmitted to the user.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform can also include an operating system and microinstruction code. The various processes and functions described herein may either be part of the microinstruction code or part of the application program (or a combination thereof) which is executed via the operating system. In addition, various other peripheral devices may be connected to the computer platform, such as an additional data storage device, and a printing device.

As a computer system, the system generally includes a processor unit. The processor unit operates to receive information, which generally includes test data (e.g., specific analytes assayed), and test result data (e.g., the profile of analytes). This information received can be stored at least temporarily in a database, and data analyzed in comparison to a library of reference analyte profiles known to be indicative of the presence or absence of a condition of interest (e.g., disease, exposure to a contaminant, etc.).

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device, and the like. Electronic forms of transmission and/or display can include email, interactive television, and the like. In one embodiment, all or a portion of the input data and/or all or a portion of the output data (e.g., usually at least the library of reference analyte profile(s) indicative of the presence or absence of a condition of interest) are maintained on a server for access, preferably confidential access. The results may be accessed or sent to professionals as desired.

A system for use with the current methods generally includes at least one computer processor (e.g., where the method is carried out in its entirety at a single site) or at least two networked computer processors (e.g., where test analyte profile data are obtained from a subject is to be input by a user (e.g., a technician or someone performing the activity assays)) and transmitted to a remote site to a second computer processor for analysis (e.g., where the test analyte profile is compared to a library of reference analyte profiles indicative of the presence or absence of a condition of interest), where the first and second computer processors are connected by a network, e.g., via an intranet or internet). The system can also include a user component(s) for input and a reviewer component(s) for review of data, generation of reports, including likely diagnosis, differential diagnosis (e.g., where the data input for the patient include clinical signs and/or symptoms) or monitoring the progression of a condition. Additional components of the system can include a server component(s); and a database(s) for storing data (e.g., as in a database of report elements, or a relational database (RDB) which can include data input by the user and data output. The computer processors can be processors that are typically found in personal desktop computers (e.g., IBM, Dell, Macintosh, etc.), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine), provides the interface to the database.

In one embodiment, the architecture is provided as a database-centric user/server architecture, in which the user application generally requests services from the application server which makes requests to the database (or the database server) to populate the report with the various report elements as desired, e.g., the best match between a test analyte profile and reference analyte profile. The server(s) (e.g., either as part of the application server machine or a separate RDB/relational database machine) responds to the user's requests.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, and offers data management, information sharing between clients, network administration, and security. The application and any databases used can be on the same or different servers.

Further embodiments encompass computing arrangements for the user and server(s), including processing on a single machine such as a mainframe, a collection of machines, or other suitable configuration. In general, the user and server machines work together to accomplish processing.

Where used, the database(s) is usually connected to the database server component and can be any device which will hold data. For example, the database can be any magnetic or optical storing device for a computer (e.g., CDROM, internal hard drive, tape drive). The database can be located remotely to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc., as desired.

Another embodiment encompasses a computer-readable storage medium (e.g., CD-ROM, memory key, flash memory card, diskette, etc.) having stored thereon a program which, when executed in a computing environment, provides for implementation of algorithms to carry out all or a portion of the methods described herein, including comparison of a test analyte profile with a reference analyte profile. Where the computer-readable medium contains a complete program for carrying out the methods described herein, the program includes program instructions for collecting, analyzing, and comparing a pattern of analyte levels to a library of reference analyte profiles indicative of the presence or absence of a condition of interest, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data may be carried out at the remote site.

The computer-readable storage medium can also be provided in combination with one or more reagents for carrying out one or more of the analyte assays (e.g., with assay test kit components).

Kits

The present disclosure also encompasses kits for practicing the current methods. The subject kits can include, for example, one or more energy application devices, LPM to liquefy tissues of interest, reagents for conducting assays of the liquefied tissue sample, and other components for carrying out the methods disclosed herein. Various compositions of LPM may be provided so that the current methods can be practiced on various tissues of interest to achieve desired results. The LPM may be provided in ready-to-use form, or may be provided as components (e.g., in separate containers) that can be mixed together to formulate the LPM suitable for the use to which the kit is to be applied. The various components of the kit may be present in separate containers, or certain compatible components may be pre-combined into a single container, as desired. The various components may also be provided treated so as to be sterile prior to use, and maintained in sterile packaging.

In addition to the above-mentioned components, the kits typically further include instructions for using the components of the kit to practice the methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step, or steps, to the objective, spirit and scope of the present invention. All such modifications are intended to be within the scope of the claims appended hereto.

Example 1

Sampling of Skin by Ultrasound

The ability of ultrasound to liquefy skin was demonstrated in vitro and quantitatively compared with the native composition profile of the skin. Liquefaction experiments were performed on porcine and human skin. Pre-cut frozen full-thickness porcine skin, harvested from the lateral abdominal region of Yorkshire pigs, was procured from Lampire Biological Laboratories Inc., PA. Frozen full-thickness human cadaver skin from healthy subjects was obtained from NDRI, NY, under the protocols approved by the Human Subjects Committee, University of California, Santa Barbara, Calif. The skin was stored at −70° C. prior to the experiment. Skin pieces with no visible imperfections, such as scratches and abrasions, were thawed at room temperature, stripped-off from subcutaneous fat, and cut into 2.5 cm×2.5 cm pieces.

Ultrasound-assisted skin liquefaction and sampling was carried out by a brief exposure of ultrasound to skin pieces mounted on a Franz diffusion cell assembly (skin exposure area of 1.77 cm$^2$). The receiver chamber of the diffusion cell was filled with phosphate buffered saline (PBS) (Sigma-Aldrich, St. Louis, Mo.) and the donor chamber was filled with 1 ml of a liquefaction-promoting solution, which also coupled the ultrasound transducer with the skin. The liquefaction-promoting medium was prepared by combining phosphate-buffered saline solution with a combination of surfactants (1% w/v sodium dodecyl sulfate (SDS), 1% (w/v) Brij-30, 1% (w/v) 1:1 mixture of N-lauroyl sarcosine (NLS) and Brij-30), and abrasive particles (0.01-1% (w/v) aluminum oxide ($AlO_2$) crystals). A protease inhibitor cocktail (P8340, Si-ma-Aldrich, St. Louis, Mo.) at a final concentration of 2% (w/v) was also added to prevent degradation of solubilized proteins. Skin sampling was performed using ultrasound transducers operating at two different frequencies. Specifically, a 600-Watt sonicator (Sonics & Materials, CT) operating at a frequency of 20 kHz and a custom-made transducer generating ultrasound at 55 kHz were used. The energy delivered to the tissue was quantified as energy fluence (J/cm$^2$), defined as the product of intensity, exposure time and duty cycle. The energy fluence range for liquefaction is 1-1000 J/cm$^2$. A range of ultrasound exposure parameters was tested. The parameters are summarized in Table 1.

In order to quantify the extent of liquefaction of skin under various experimental conditions, the total amount of proteins present in the LPM was measured. Ultrasound-assisted liquefaction of porcine skin yielded up to 0.65±0.10 mg proteins per cm$^2$ of sampled skin as compared to 0.045±0.001 mg proteins per cm$^2$ of skin that was incubated with the liquefaction medium without ultrasound exposure, indicating that ultrasonic energy greatly facilitated liquefaction of skin constituents. Ultrasound-assisted liquefaction of human skin yielded up to 0.42±0.03 mg/cm$^2$ of proteins. Table 1 shows the protein concentration in liquefied porcine and human skin samples at various ultrasound conditions and liquefaction solution compositions. Notably, liquefaction solution consisting of 1% (w/v) 1:1 surfactant mixture of NLS and Brij-30 was most synergistic with ultrasound for liquefying skin constituents.

The liquefaction medium was further characterized for the presence of different native analyte classes that exist in skin. For this purpose, liquefaction medium containing 1% (w/v) SDS was obtained by applying ultrasound at a fluence of 216 J/cm$^2$. Liquefaction solution was subjected to 1-dimensional SDS-PAGE in a polyacrylamide gel (7.5%) system (FIG. 1, Panel a, for porcine skin and Panel b for human skin) to ascertain protein profiles separated on the gel according to different molecular weights. Protein extract prepared by homogenizing heat-stripped whole epidermis (FIG. 1, Panel a, lane 1) was used as a positive control. A high congruence between the protein migration patterns of the ultrasonically liquefied sample (lane 2) and native proteins expressed in epidermal layers of skin (lane 1) was observed (FIG. 1, Panel a). Similarly, a high congruence was also seen for profiles of ultrasonically liquefied human skin proteins (lane 2) and heat-stripped human epidermis (lane 1) (FIG. 1, Panel b).

Western blot analysis of the ultrasound-liquefied pig and human skin was performed to detect the presence of various key cytoskeletal and cytoplasmic skin proteins. Specifically, both pre-keratin and keratin filament subfamilies, which constitute the majority of cytoskeletal proteins in the epidermis, were detected in the porcine ultrasound samples (FIG. 1, Panel c, lane 1). As shown in FIG. 1, Panel c, these profiles matched with those found in the whole epidermis samples (lane 2). Ultrasonically liquefied human skin samples confirmed the presence of many keratin families, such as K1, K5, K10, K14 and K19 (lane 1, FIG. 1, Panel d), as observed in human skin homogenate (lane 2). Further,

TABLE 1

Quantification of proteins in skin samples obtained by ultrasonic energy

| Ultrasound Exposure Parameters | | | | | | Protein |
|---|---|---|---|---|---|---|
| Frequency [kHz] | Exposure Time [s] | Duty Cycle [%] | Fluence [J/cm$^2$] | Skin Type | LPM Composition | Concentration [mg/cm$^2$] |
| 20 | 90 | 50 | 108 | Porcine | 1% (w/v) SDS | 0.15 ± 0.03 |
| 20 | 90 | 50 | 108 | Porcine | 0.01% (w/v) $AlO_2$ 1% (w/v) SDS | 0.18 ± 0.04 |
| 20 | 90 | 50 | 108 | Porcine | 0.1% (w/v) $AlO_2$ 1% (w/v) SDS | 0.28 ± 0.11 |
| 20 | 90 | 50 | 108 | Porcine | 1% (w/v) $AlO_2$ 1% (w/v) SDS | 0.13 ± 0.02 |
| 20 | 30 | 100 | 72 | Porcine | 1% (w/v) SDS | 0.10 ± 0.05 |
| 20 | 90 | 100 | 216 | Porcine | 1% (w/v) Brij-30 | 0.14 ± 0.07 |
| 20 | 90 | 50 | 108 | Porcine | 1% NLS/Brij-30 | 0.65 ± 0.10 |
| 20 | 90 | 50 | 108 | Human | 1% (w/v) SDS | 0.41 ± 0.22 |
| 55 | 30 | 100 | 300 | Porcine | 1% (w/v) SDS | 0.18 ± 0.05 |
| 55 | 40 | 100 | 108 | Porcine | 1% NLS/Brij-30 | 0.42 ± 0.03 | cytoplasmic proteins including major heat-shock protein families (hsp60—FIG. 1, Panel e and hsp70—FIG. 1, Panel f) and β-actin (FIG. 1, Panel g) were also detected in porcine ultrasound samples (lane 1) as compared with the positive control—whole epidermis protein samples (lane 2).

Sixteen types of non-polar and polar lipids were also detected in ultrasonic samples obtained from porcine skin. A lipid sample obtained by homogenizing porcine stratum corneum was used as a positive control. Thin-layer chromatographs of both non-polar lipids (FIG. 1, Panel h) and polar lipids (FIG. 1, Panel i) demonstrate a high resemblance in lipid profiles obtained from ultrasound liquefied skin samples (US) and lipids isolated from stratum corneum (SC).

Ultrasound liquefaction liberated several key natural moisturizing factors (NMFs) that are present in pig skin. NMFs, which are derived from enzymatic degradation of the filaggrin molecule in skin, are responsible for skin's hydration, regulation of water flux, and its flexibility and strength. NMFs consist of several types of small molecules, of which free amino acids, lactate, and urea (amounting to about 60% of the total NMFs present in the skin) were analyzed. Deproteinized samples from porcine stratum corneum and ultrasound samples were prepared by treatment with 2% trichloroacetic acid. A comparative analysis of stratum corneum samples revealed that ultrasound-assisted sampling significantly captured the naturally occurring profile of free amino acids present in the skin (FIG. 1, Panel j). Table 2 shows a quantitative estimate and statistically significant congruence in the free amino acid profiles from the samples. Using enzymatic detection kits, L-lactic acid and urea concentrations in the ultrasonic skin samples were found to be $0.013 \pm 0.001$ g/L and $0.148 \pm 0.054$ mg/dL respectively.

TABLE 2

Natural Moisturizing Factors: Free amino acid profile

| Amino Acid | Ultrasound Sample [%] | Stratum Corneum [%] | p value |
| --- | --- | --- | --- |
| Hydroxy praline (hyp) | 33.86 ± 12.75 | 28.98 ± 3.82 | 0.58 |
| Aspartic acid (asp) | 20.60 ± 4.68 | 16.83 ± 1.81 | 0.30 |
| Serine (ser) | 10.67 ± 4.13 | 14.33 ± 1.37 | 0.26 |
| Glutamic acid (glu) | 1.28 ± 0.56 | 2.61 ± 0.22 | 0.04 |
| Proline (pro) | 2.66 ± 1.44 | 3.62 ± 0.42 | 0.37 |
| Glycine (gly) | 5.74 ± 2.05 | 5.94 ± 0.63 | 0.88 |
| Alanine (ala) | 3.67 ± 1.33 | 3.30 ± 0.33 | 0.68 |
| Cysteine (cys) | 0.70 ± 0.41 | 1.06 ± 0.11 | 0.27 |
| Isoleucine (ile) | 0.45 ± 0.18 | 0.54 ± 0.06 | 0.49 |
| Leucine (leu) | 0.90 ± 0.34 | 0.89 ± 0.12 | 0.95 |
| Tyrosine (tyr) | 0.53 ± 0.26 | 0.71 ± 0.08 | 0.37 |
| Phenylalanine (phe) | 0.52 ± 0.22 | 0.68 ± 0.07 | 0.32 |
| Histidine (his) | 2.37 ± 0.83 | 5.08 ± 0.45 | 0.01 |
| Lysine (lys) | 0.86 ± 0.36 | 0.89 ± 0.11 | 0.93 |
| Arginine (arg) | 2.25 ± 0.64 | 3.66 ± 0.29 | 0.04 |

(p value represents the level of significance obtained using student's t test)

The ultrasound-assisted liquefaction method liberated $167.9 \pm 71.0$ ng/cm$^2$ of nucleic acids from porcine skin. Two separate fractions containing RNA and DNA were fractionated from the solution using Trizol LS (Invitrogen, Carlsbad, Calif.) and electrophoretically migrated on an agarose gel system. Fluorescent staining of gels with SYBR Gold stain (Invitrogen, Carlsbad, Calif.) confirmed their specific presence.

Example 2

Sampling of Mucosal Membranes Using Ultrasonic Energy

Figures 3A, 3B, 3C, 3D:
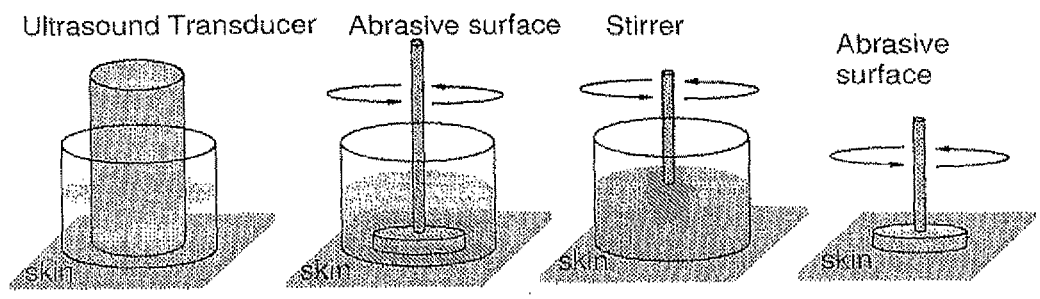
FIG. 3 (Panels a-e) is a collection of schematics exemplifying different methods for applying energy to liquefy tissues; (a) ultrasound, (b) abrasive surfaces in conjunction with liquefaction promoting medium, (c) high-speed stirring of liquefaction promoting medium, (d) use of absorbent abrasive discs, and (e) abrasion by a high-velocity stream comprising a gaseous mixture of abrasive particles.
Figure 3E:
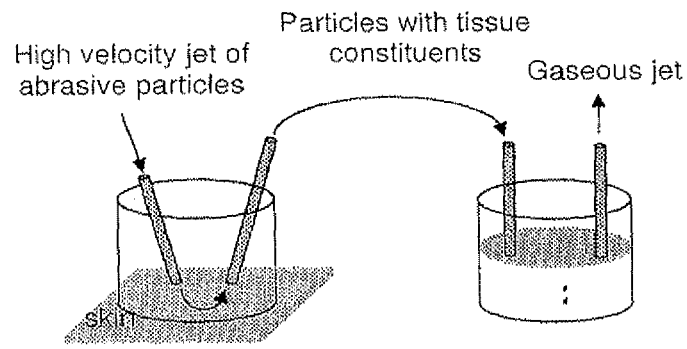

The ability of ultrasonic energy to liquefy three mucosal membranes was demonstrated in vitro and was quantitatively compared with the native composition profile of the tissue. Specifically, experiments were performed on colon, nasal, and buccal mucosal membranes from pigs. Frozen porcine mucosal tissues were procured from Siena-Medical, Whittier, Calif. Tissues with no visible imperfections were cut into small pieces (2.5 cm×2.5 cm) and stored at −70° C. Ultrasound-assisted liquefaction was carried out by a brief exposure of ultrasound to tissues mounted on a Franz diffusion cell assembly as outlined in Example 1. Ultrasonic energy was applied at 20 kHz and energy fluence of 72 J/cm$^2$. A solution containing 1% (w/v) SDS in PBS was used as the liquefaction-promoting medium. FIG. 3, Panel a provides a schematic of the ultrasound application to the tissue.

Ultrasonic energy greatly facilitated liquefaction and sampling of mucosal tissue constituents. Table 3 provides, for each mucosal tissue, a quantitative assessment of the solubilized proteins per cm$^2$ of tissue.

TABLE 3

Quantification of proteins in mucosal tissue samples obtained by ultrasonic energy

| Tissue Type | Protein Concentration [mg/cm$^2$] |
| --- | --- |
| Colon mucosa | 1.21 ± 0.16 |
| Buccal mucosa | 0.19 ± 0.05 |
| Nasal mucosa | 2.47 ± 2.44 |

Figures 2A, 2B, 2C:
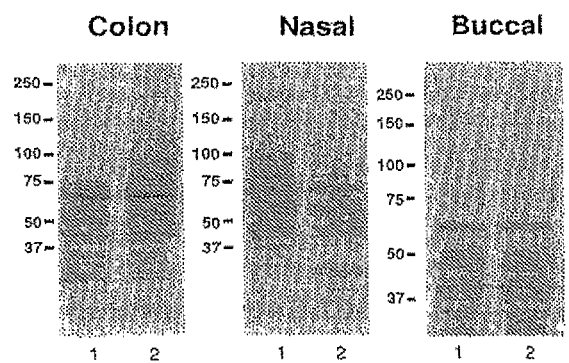
FIG. 2 (Panels a-e) is a collection of photographs illustrating: characterization of proteins isolated from colon (Panel a), nasal (Panel b), and buccal mucosa (Panel c) by homogenizing the tissue (lane 1), and using ultrasonic liquefaction (lane 2); thin layer chromatography of polar lipids (Panel d) and non-polar lipids (Panel e) isolated from homogenates of porcine mucosa (lane "MU") and lipid enriched ultrasound liquefaction from respective tissue (lane "US").
Figure 2D:
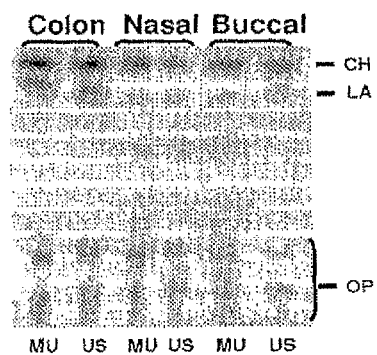
Figure 2E:
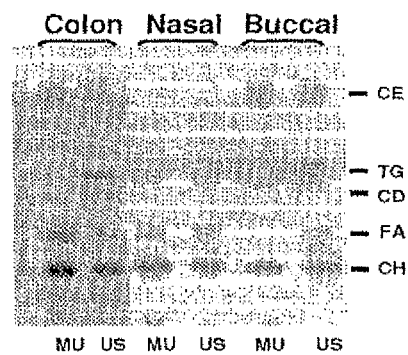

One-dimensional SDS-PAGE (FIG. 2; Colon—Panel a, Nasal—Panel b, and Buccal—Panel c) further showed a high similarity in protein profiles of ultrasound samples (lane 2) with protein samples prepared from mucosal tissue homogenates (lane 1). Nine types of lipids were also detected in ultrasonic samples of mucosal membranes. A lipid sample obtained from homogenizing respective tissue was used as a positive control for comparison purposes. Thin-layer chromatographs of both polar lipids (FIG. 2, Panel d) and non-polar lipids (FIG. 2, Panel e) demonstrate a resemblance in lipid profiles obtained from ultrasound-exposed skin sample (US) and lipids isolated from mucosal tissue homogenate (MU).

Example 3

Sampling of Skin Using Abrasive Devices

The ability to liquefy skin by applying rotating abrasive surfaces held in contact with skin was demonstrated. Four representative abrasive surfaces were used in this study—a) a circular disc made of felt fabric (contact area: 0.8 cm$^2$), b) a solid circular disc made of AlO$_2$ crystals (contact area: 0.6 cm$^2$), c) 600 grit-size silicon carbide sand paper (contact area: 1.12 cm$^2$), and d) a circular brush with plastic bristles (contact area: 0.2 cm$^2$). Liquefaction experiments were performed on porcine skin by mounting skin pieces on a Franz diffusion cell assembly as outlined in Example 1. Specifically, the donor chamber of the diffusion cell was filled with 1 ml of a liquefaction-promoting medium, and the rotating abrasive surface was introduced in the donor chamber such that it directly contacted the skin sample (see schematic in FIG. 3, Panel b). As the liquefaction procedure proceeded, the abraded skin constituents were simultaneously dissolved in the solution. Various formulations of liquefaction solution were used, including pure phosphate-buffered saline (PBS), and PBS comprising 1% w/v sodium dodecyl sulfate (SDS), 1% (w/v) 1:1 mixture of N-lauroyl sarcosine (NLS) and Brij-30), and 0.01-1% (w/v) aluminum oxide ($AlO_2$) crystals. A protease inhibitor cocktail (P8340, Si-ma-Aldrich, St. Louis, Mo.) at a final concentration of 2% (w/v) was also added to the solution to prevent degradation of solubilized proteins. Table 4 summarizes the abrasion parameters used, the composition of the liquefaction-promoting solution, and the protein concentration that was measured in the solution after the procedure.

Abrasive devices (mentioned in Table 4) greatly facilitated liquefaction of skin constituents. In order to quantify the extent of liquefaction of skin under different experimental conditions, the total amount of proteins present in the solution was measured. Abrasion-assisted liquefaction of porcine skin yielded up to 2.02±0.10 mg of proteins per $cm^2$ of skin.

and liquefaction solution containing 1% (w/v) $AlO_2$ crystals, 0.04±0.01 mg of proteins per $cm^2$ were liquefied from exposed skin.

Yet another method for applying abrasive forces to sample tissues is the use of a high-velocity jet comprising a gaseous mixture of abrasive particles such as $AlO_2$ crystals. In such a method, the jet, when directed towards the tissue of interest, can dislodge tissue constituents and carry them with it to a container holding liquefaction solution, and in the process dissolve the tissue constituents in the solution (see schematic in FIG. 3, Panel e). The solution can then be analytically processed using methods such as ELISA, mass spectrometry, chromatography, and/or spectrophotometry to detect the presence or absence of one or more tissue analytes.

Example 4

Microflora Detection in Skin

Tissues, particularly skin and mucosal membranes, are a host for multiple microorganisms including several families of bacteria. Current methodologies for microflora detection

TABLE 4

Quantification of skin samples obtained by abrasive devices

| Abrasion Method | Abrasion Parameters | | | Protein Concentration [mg/cm$^2$] |
|---|---|---|---|---|
| | Exposure Time [s] | Contact Pressure [N/m$^2$] | LPM Composition | |
| Felt-fabric Disk | 10 | 16375 | PBS | 0.07 ± 0.03 |
| AlO$_2$ Disk | 10 | 16375 | PBS | 0.36 ± 0.05 |
| | 20 | 16375 | PBS | 0.39 ± 0.03 |
| | 30 | 16375 | PBS | 0.43 ± 0.09 |
| | 30 | 33245 | PBS | 0.01 ± 0.00 |
| | 30 | 33245 | 1% (w/v) AlO$_2$, 1% (w/v) SDS in PBS | 0.08 ± 0.01 |
| | 30 | 33245 | 1% (w/v) AlO$_2$ in PBS | 0.04 ± 0.03 |
| | 60 | 33245 | 1% (w/v) AlO$_2$ in PBS | 0.02 ± 0.01 |
| | 10 | 1662 | 1% NLS/Brij-30 in PBS | 0.53 ± 0.01 |
| | 10 | 3325 | 1% NLS/Brij-30 in PBS | 0.31 ± 0.07 |
| Brushing Device | 10 | 5770 | 1% NLS/Brij-30 in PBS | 2.02 ± 0.10 |
| | 10 | 11541 | 1% NLS/Brij-30 in PBS | 1.20 ± 0.23 |
| Sanding Paper | 5 | 9806 | 1%(w/v) SDS in PBS | 0.30 |

A variation to the method described above for sampling tissues with abrasive surfaces is the use of an "absorbent" abrasive fabric pad which can simultaneously abrade as well as absorb the dislodged tissue constituents in it, offering a simple and patient-friendly means for tissue sampling (see schematic in FIG. 3, Panel d). The abrasive pad can be analytically processed for the presence or absence of one or more tissue analytes.

Figure 4:
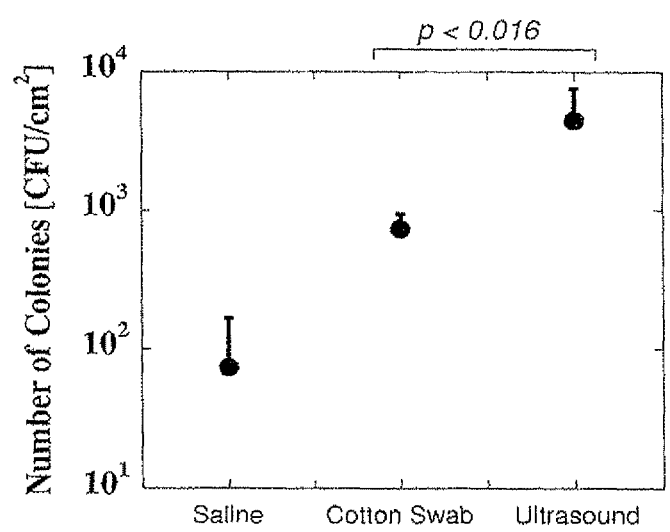
FIG. 4 is a graph illustrating the number of colonies grown on agar plates from samples obtained by phosphate buffered saline (PBS) scraping, swabbing, and ultrasound liquefaction.
Figure 5A:
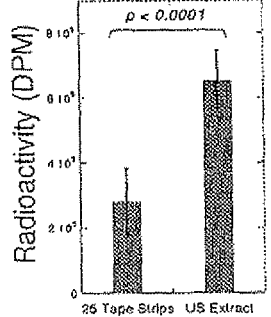
FIG. 5 (Panels a-d) is a collection of graphs illustrating liquefaction of behinol or fluconazole. Panel a shows the amount of behinol extracted from skin using 25 consecutive tape strips compared with ultrasound-liquefied samples. Panel b shows the amount of behinol extracted from skin obtained by using 25 consecutive tape strips compared with ultrasound liquefaction when the drug was administered from the dermis side of the skin for 8 hours (grey bars) and 24 hours (black bars). Panel c shows the fluconazole bioavailability as determined through ultrasound liquefaction, tape stripping, wipe testing, and blood testing. Panel d shows the percentage of cocaine bioavailability as determined through ultrasound liquefaction, tape stripping, and urine testing.
Figure 5B:
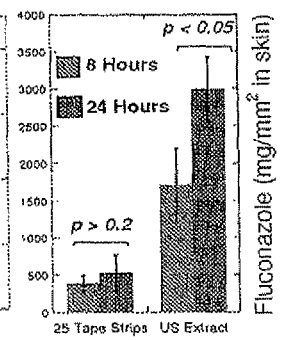
Figure 5C:
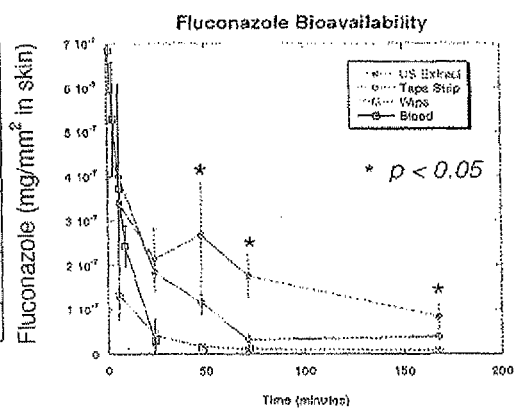
Figure 5D:
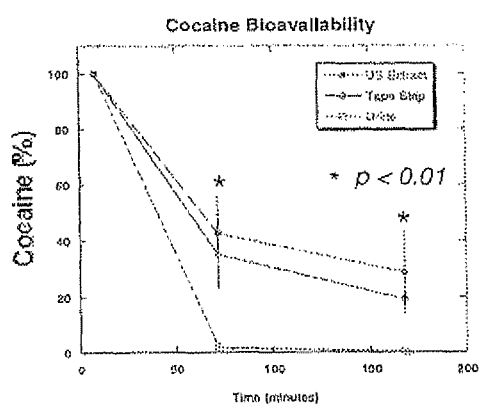
Figure 6A:
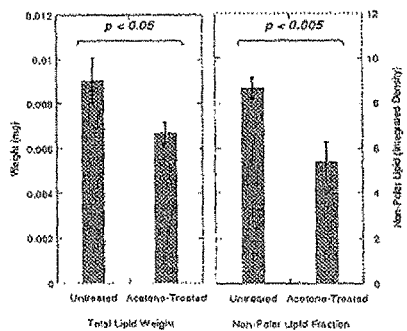
FIG. 6 (Panels a-d) is a collection of graphs. Panel a illustrates the amount of total lipid weight present in untreated v. acetone treated skin, as well as the non-polar lipid fraction present in untreated v. acetone treated skin. Panel b illustrates the thin layer chromatography analysis of samples from Panel a (C=ultrasound liquefaction from normal skin; AE=acetone extract; A=ultrasound liquefaction from acetone-treated skin). Panel c illustrates ultrasound-assisted profiling of acetone-induced upregulation of skin cytokines, classified in groups according to their functionality, as compared to untreated skin. Panel d illustrates quantitative analysis of specific cytokines in acute barrier disruption of skin.
Figure 6B:
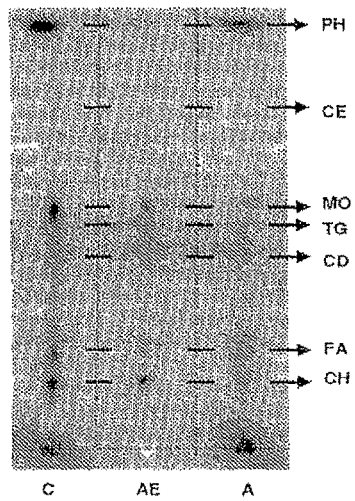
Figure 6C:
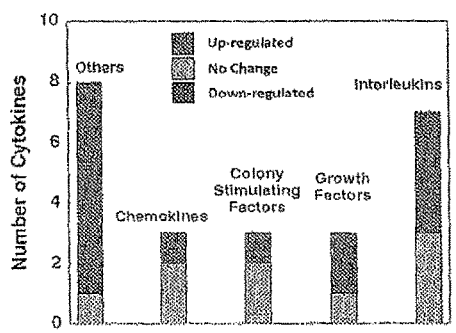
Figure 6D:
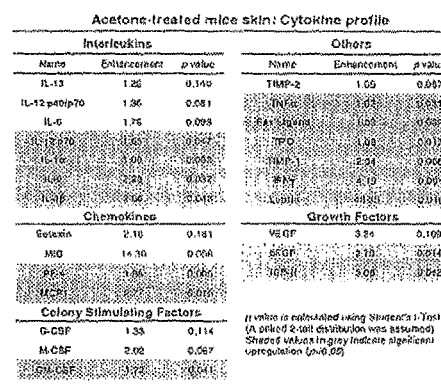
Figure 7A:
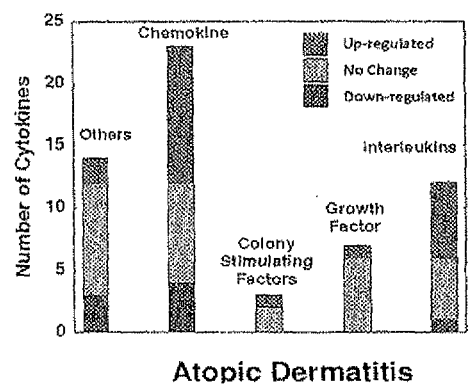
FIG. 7 (Panels a-d) is a collection of graphs and photographs illustrating the following: a comprehensive distribution of ultrasonically liquefied cytokines present in skin with atopic dermatitis ("AD") (Panel a) and psoriasis ("PS") (Panel b); thin layer chromatography of ultrasonically sampled lipids for healthy skin (lane C), AD skin (lane AD), and PS skin (lane PS) (Panel c); an immunoblot for IgG antibodies present in PS, AD, and healthy skin (C) (Panel d).
Figure 7B:
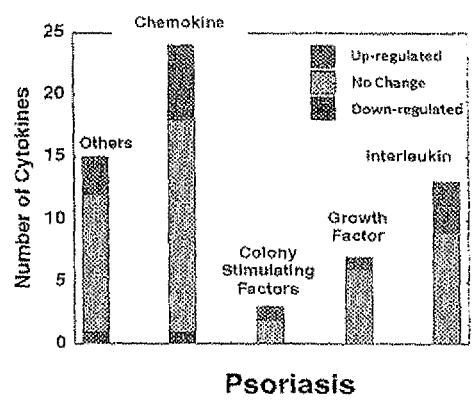
Figure 7C:
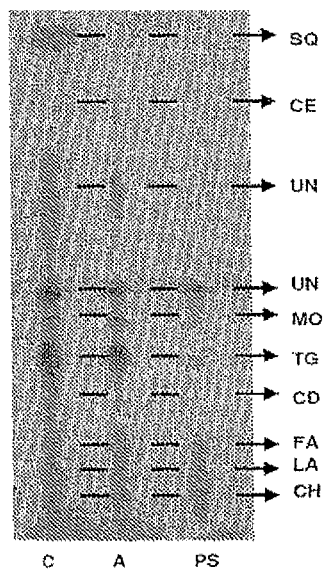
Figure 7D:
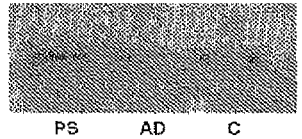

Another method to apply abrasive force for sampling tissue constituents was demonstrated by using a liquid stirrer. As described in FIG. 3, Panel c, this comprises placing liquefaction solution, containing abrasive particles and/or surfactants, in contact with tissue and applying abrasive force by high-speed stirring of the solution. In an in vitro setting utilizing a stirrer rotating at a speed of 5000 rpm in accessible tissues, such as replica plating, swabbing, and washing, are unattractive due to large variability and low dispersion of extracts, leading to decreased sensitivity and high protocol-dependency. FIG. 4 demonstrates that brief exposure to ultrasonic energy can extract viable and naturally occurring bacteria from skin in a saline solution. To compare this methodology, saline solutions obtained from various procedures were tested for plating-efficiency on agar plates. Bacterial colonies obtained from ultrasonic sampling were significantly larger than those obtained from swabbing the skin with cotton balls. Further analysis for bacterial characterization revealed the presence of several skin-specific bacteria, such as *Staphylococcus* sp. and *Micrococcus* sp., in the ultrasound-collected samples. Incubation of skin with saline (without ultrasound exposure) collected significantly fewer bacteria from skin.

Example 5

Pharmacokinetic Evaluation of Therapeutics and Detection of Drugs-of-Abuse in Skin Systemic drug bioavailability does not necessarily depict the concentration of therapeutic drugs in tissues. In this example, ultrasound-assisted tissue liquefaction was performed to assess the drug bioavailability in skin and detect drugs-of-abuse for forensics. In vitro experiments using Franz diffusion cells were designed to topically deliver the antiviral drug behinol (at donor concentration of 10 µCi/ml for 4 hrs.) or to mimic systemic administration of behinol from the dermis side of porcine skin (at receiver concentration of 1 µCi/ml for 8 and 24 hrs). For topically delivered behinol, ultrasound-assisted liquefaction increased the amount of sampled drug by 2.42±0.47 fold (p<0.001, Students' t-test) compared to solubilization through sequential tape stripping (25 times) of the skin (a conventionally used method) (FIG. 5, Panel a). The tape stripping procedure did not distinguish between 8 hours of exposure (grey bars) and 24 hours of exposure (black bars) when behinol was delivered from the dermis side of the skin (p>0.2: Student's t-test; FIG. 5, Panel b). However, ultrasonic sampling showed a significant increase in the amount of collected drug as compared to the tape stripping procedure, and was also able to distinguish between drug delivered to the skin for 8 hours and for 24 hours (p<0.05, Student's t-test).

The transdermal detection of intravenously administered drugs was performed in vivo in Sprague Dawley rats. The rats were anesthetized using 1.25-4% isofluorane in oxygen and were intravenously administered with 10 mg/kg (250 µCi/kg) of an antifungal drug, fluconazole, or 5 mg/kg (175 µCi/kg) of an abused drug, cocaine, by tail vein injections in two separate experiments. The drugs were collected from skin on the back of the animals at various times after the injection using the ultrasound-assisted tissue liquefaction procedure at 20 kHz, 360 J/cm². Blood samples, taken from the jugular vein, were collected for comparison purposes, and urine samples were also collected and analyzed. Topical skin swabs were carried out as controls, and cyanoacrylate-assisted tape stripping was performed as a comparison to the ultrasound-assisted tissue liquefaction procedure. Blood levels of fluconazole rapidly fell to radioactively-undetectable concentrations (9.66×10-7 mg/ml) in 24 hours, but fluconazole was consistently and significantly detected in the skin for over 7 days after administration as determined by cyanoacrylate-tape stripping (FIG. 5, Panel c). Ultrasound-assisted tissue liquefaction detected fluconazole in the skin, and occasionally the concentration was significantly higher than the concentration detected by the tape stripping procedure (p<0.05, FIG. 2, Panel c). Skin swabs did not detect any substantial amount of the drug in skin.

Ultrasound-assisted tissue liquefaction of cocaine was tested as an application for forensic detection of drugs-of-abuse. FIG. 5, Panel d shows the percentage of cocaine remaining in skin and urine as a function of time. Cocaine levels rapidly fell to less than 0.25% in urine samples; however, a sustained presence of cocaine was detected in skin using ultrasound-assisted tissue liquefaction for up to 7 days after drug administration.

Example 6

Evaluation of Skin Diseases by Quantifying Biomolecular Changes

To demonstrate ultrasound-assisted tissue liquefaction as a sensitive diagnostic technique, the procedure was performed on three different in-vivo animal models that mimic various skin diseases. The in vivo animal models were a) acetone-challenged mouse skin model, b) atopic dermatitis mouse model, and c) psoriasis (flaky skin) mouse model. The unique tissue constituent profiles obtained from these animal models were quantitatively compared with profiles from healthy skin to demonstrate that the tissue liquefaction technique could effectively diagnose each condition.

SKH1 hairless mice aged 5-8 weeks were purchased from Charles River Laboratory, Wilmington, Mass. Acute barrier disruption was induced in the skin of the hairless mice by treating the flank skin with absolute acetone, while the other flank skin was used as a control site. One ml of acetone was placed on the skin for 15 min in experiments examining cytokine upregulation and for 30 minutes to quantify changes in the skin's lipid composition. Ultrasound-assisted tissue liquefaction was performed on 1.3 cm² of exposed skin, using parameters of 20 kHz, 360 J/cm², and a liquefaction medium of 1% SDS. Analysis of the samples detected a significant decrease in total skin lipid weight (1.35-fold, p<0.05, FIG. 6, Panel a) and a simultaneous decrease in non-polar lipid weight was also observed (1.65-fold. p<0.005, FIG. 6, Panel a). This was confirmed using thin layer chromatographs (FIG. 6, Panel b) of lipids present in acetone-treated skin samples (lane A), acetone extract (lane AE) and normal skin (lane C). Acetone, an organic solvent, specifically extracted non-polar skin lipids such as methyl oleate (MO), triglycerides (TG) and cholesterol (CH), while polar lipids remained largely unaffected (data not shown) in the acetone-challenged mice skin.

Ultrasound also captured acetone-induced upregulation of inflammatory cytokines as compared to untreated skin extracts (FIG. 6, Panel c). Twenty four cytokines were simultaneously detected in a sandwich-ELISA-based antibody array assay (ChemiArray™ Mouse Antibody Arrays kit—AA2001GM, Chemicon, Temecula, Calif.) that was performed according to the manufacturer's instructions. Ultrasound-assisted tissue liquefaction samples contained several key cytokines that are implicated in acute barrier disruption of skin. These cytokines were significantly upregulated (p<0.05, FIG. 6, Panel d).

FIG. 6, Panel c categorizes these signaling proteins into groups according to their functionality, enabling a unique cytokine profile representation of acetone-challenged skin. Altered lipid and cytokine profiles of mice suffering from atopic dermatitis (AD) and psoriasis (PS) were quantified and compared to healthy mice. Five week old mice homozygous for the flaky skin mutation (strain: CByJ.A-Ttc7fsn/J, Jackson Laboratory, ME) were used as animal models for psoriasis. Ten week old NC/NgaTndCrlj mice from Charles River Laboratory, Japan, were used as an animal model for atopic dermatitis. To initiate atopic dermatitis, a topical formulation consisting of 0.15% (v/v) 2,4-dinitrofluorobenzenein acetone/olive oil (3:1 v/v) was repeatedly applied once a week for 6 weeks on the skin of NC/Nga mice. Balb/c mice having the same age as the respective diseased mice were used as controls. All animal handling and maintenance protocols were approved by the Institutional Animal Care and Use Committee, University of California, Santa Barbara, Calif. A cytokine array assay, probing for 62 signaling proteins (AA2003M, Chemicon, Temecula, Calif.), was used to quantify up or down-regulation of cytokines in AD and PS mice.

FIG. 7, Panel a (for AD) and Panel b (for PS) shows a comprehensive distribution of ultrasonically collected cytokines, creating unique cytokine maps for AD and PS skins. Specific enhancement ratios for each cytokine, categorized as interleukins, chemokines, growth factors, colony stimulating factors, and others are listed in FIG. 9 for AD and FIG. 10 for PS mice.

Thin layer chromatography was performed to evaluate if ultrasonically sampled lipids could depict changes in lipid profiles of AD and PS. FIG. 7, Panel c shows migration of lipids on silica gel for healthy (lane C), AD (lane AD) and PS (lane PS) skin. A significant reduction of non-polar lipids including squalene and cholesteryl esters in AD and PS mice skin was observed ($p<0.05$, FIG. 11). Upregulation of polar lipids for AD, specifically lanosterol, and cholesterol in PS skin were seen ($p<0.05$, FIG. 11). FIG. 11 shows a quantitative and distinct profile of down-regulated non-polar lipids and upregulated polar lipids, which is consistent with the breached barrier properties of skin in these diseases.

Further, antibodies as biomarkers for cutaneous pathogenesis were examined in the ultrasonically liquefied samples. FIG. 7, Panel d shows an immunoblot specific for IgG antibodies present in diseased (AD and PS) and healthy (C) skin. Both AD and PS showed a marked increase in the amount of IgG liquefied from skin (normalized by total protein weight of extract) when compared to healthy skin samples. This observation is consistent with the presence of immuno-deposits in disease, particularly psoriasis.

Example 7

Liquefaction Promoting Medium

The ability of several known surfactants and surfactant mixtures to act as a liquefaction promoting medium in presence of ultrasound was tested. The ability of these media to sample tissues was quantified in terms of the amount of protein extracted from porcine skin and the ability of these media to retain protein activity was quantified by measuring concentration of IgE antibodies that were added to the medium.

Supernatants were isolated from liquefied skin samples with centrifuge at 20,000 g at 4 C for 20 min. The protein concentration of the samples was measured by using a colorimetric detection kit (Micro BCA Protein Assay Kit, Pierce). The calibration curve was obtained using freshly prepared Bovine Serum Albumin standards diluted in the Liquefaction Promoting Medium corresponding to the sample. Protein concentration was determined by dividing total protein content of the sample with tissue area.

ELISA technique was used to determine the binding ability of IgE antibodies with their specific antigen, after antibodies had been incubated with various liquefaction-promoting media for 10 minutes. Specific IgE antibodies against Chicken Ovalbumin (OVA) were used. 100 micrograms of OVA was coated per well of a 96 well plate. IgE antibodies were dissolved in various surfactant solutions (LPMs) at a concentration of 1 microgram/ml. After a 10 minute incubation with a blocking buffer, IgE-LPM solutions were incubated in the wells for 1 hour. After washing the wells, HRP-linked-secondary antibody at a concentration of 2 microgram/ml was incubated in each well for 1 hour. After washing, a HRP-based signal was obtained using spectrophotometry. For each LPM the % activity was calculated by comparing with the positive control (ie, IgE in PBS—no surfactant).

Figure 8:
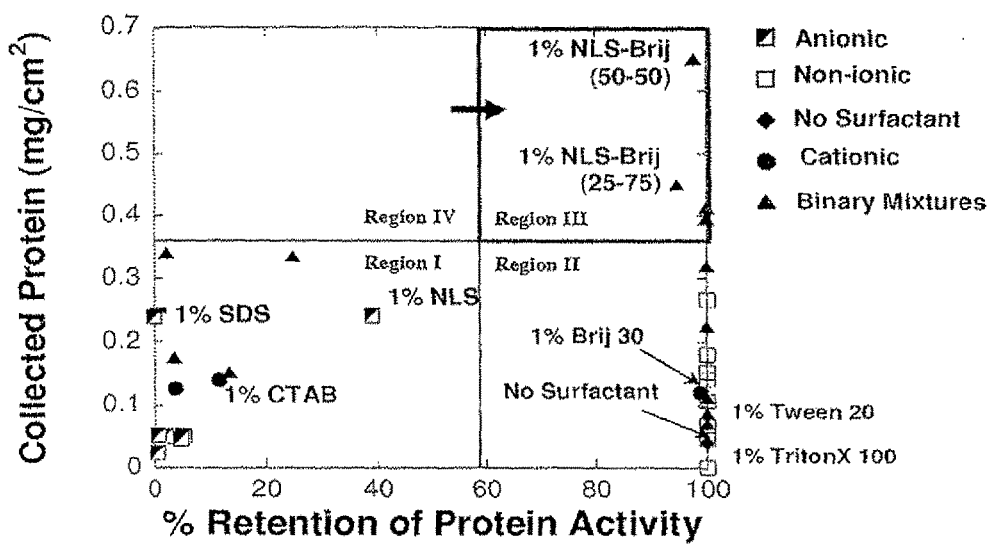
FIG. 8 is a graph illustrating the effects of various liquefaction promoting agents on the total amount of proteins sampled by ultrasonic liquefaction from porcine skin, as well as the percent residual biological activity of the proteins in the liquefied skin sample.
Figure 12:
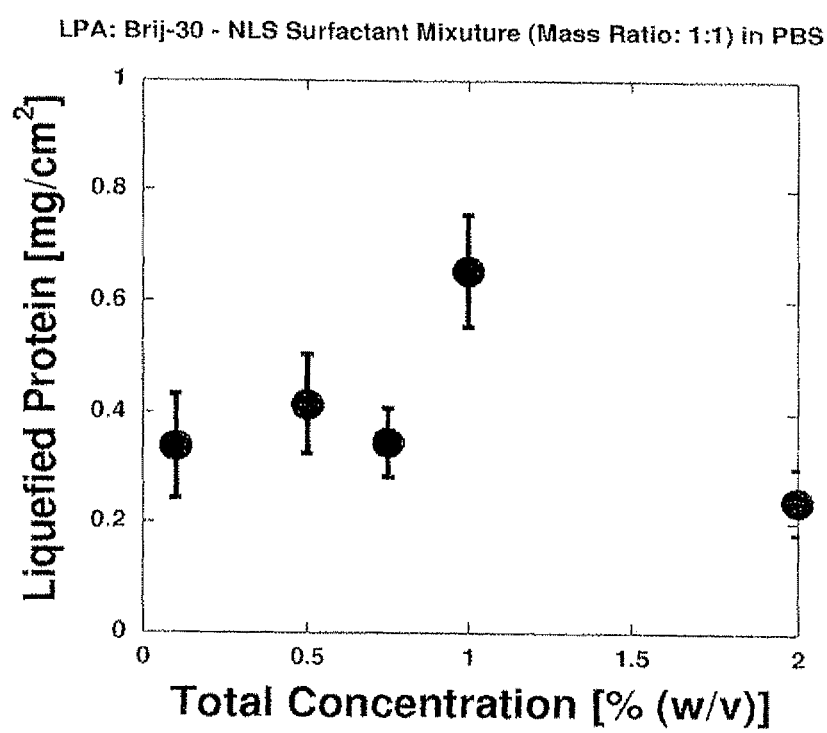
FIG. 12 is a graph showing the results of analysis of different concentrations of surfactants on liquefaction of protein.

The results are provided in the table below; selected results are provided in the graph of FIG. 8.

| | IgE denaturation/binding affinity in the presence of surfactants Reading at 10 min | | | |
|---|---|---|---|---|
| Surfactant Type | Surfactant Name | | Bio-Activity % | Protein Liquefaction (mg/cm2) |
| Anionic | Ammonium lauryl sulfate | A1 | 5.28 | 0.051 |
| | Decyl sodium sulfate | A2 | 2.05 | 0.051 |
| | Na Tetradecyl sulfate | A3 | 0.56 | 0.024 |
| | Sodium octyl sulfate | A4 | 0.73 | 0.052 |
| | Triethanolamine lauryl sulfate | A5 | 4.80 | 0.047 |
| Cationic | Dodecylpyridium chloride | C1 | 3.93 | 0.127 |
| | Octyltrimethylammonium bromide | C2 | 98.85 | 0.120 |
| | C12TAB | C3 | 11.69 | 0.140 |
| | BDAC | C4 | 28.91 | ANC* |
| | Alkyldimethyl chloride | C5 | 100.00 | ANC |
| Non-ionic | Brij 35 | N1 | 100.00 | 0.141 |
| | Brij 56 | N2 | 100.00 | 0.180 |
| | Brij 97 | N3 | 100.00 | ANC |
| | NP-9 | N4 | 100.00 | 0.267 |
| | Peg 200 | N5 | 100.00 | 0.107 |
| Anionic-Cationic 50:50 | Mixture of A1 with C1 | AC1 | 13.49 | 0.15 |
| | Mixture of A2 with C2 | AC2 | 100.00 | 0.11 |
| | Mixture of A3 with C3 | AC3 | 100.00 | 0.07 |
| | Mixture of A4 with C4 | AC4 | 100.00 | 0.09 |
| | Mixture of A5 with C5 | AC5 | 75.94 | ANC |
| Anionic--Non-ionic 50:50 | Mixture of A1 with N1 | AN1 | 100.00 | 0.22 |
| | Mixture of A2 with N2 | AN2 | 2.39 | 0.34 |
| | Mixture of A3 with N3 | AN3 | 98.15 | ANC |
| | Mixture of A4 with N4 | AN4 | 100.00 | 0.39 |
| | Mixture of A5 with N5 | AN5 | 3.77 | 0.17 |
| Cationic--Non-ionic 50:50 | Mixture of C1 with N1 | CN1 | 24.89 | 0.33 |
| | Mixture of C2 with N2 | CN2 | 100.00 | 0.41 |
| | Mixture of C3 with N3 | CN3 | 92.03 | ANC |
| | Mixture of C4 with N4 | CN4 | 26.54 | ANC |
| | Mixture of C5 with N5 | CN5 | 65.69 | ANC |

-continued

IgE denaturation/binding affinity in the presence of surfactants
Reading at 10 min

| Surfactant Type | Surfactant Name | | Bio-Activity % | Protein Liquefaction (mg/cm2) |
|---|---|---|---|---|
| Other Non-ionic | S20 (SPAN) | S20 | 100.00 | 0.047 |
| | Brij 30 | Brij | 100.00 | 0.153 |
| | Tween-20 | Tween | 100.00 | 0.07 |
| | Triton X-100 | TritonX | 100.00 | 0.00 |
| Other Anionic | NLS | NLS | 38.99 | 0.242 |
| | SLS (aka SDS) | SLS | 0.00 | 0.240 |
| Other Binary | Brij30-NLS 50:50 | Brij-NLS 50:50 | 97.81 | 0.650 |
| | Brij30-NLS 75:25 | Brij-NLS 75:25 | 100.00 | 0.320 |
| | Brij30-NLS 25:75 | Brij-NLS 25:75 | 94.77 | |

*ANC = "Assay not compatible" Indictaes that total protein concentration could not be measured due to the nature of the sample matrix and associated technical limitations. This is not meant to indicate that no protein was present.

The tested media can be classified into four regions as illustrated in FIG. 8. Region I corresponds to media that cannot sample large quantities of protein and cannot retain biological activity. Region II indicates media that cannot sample large quantities of proteins but retain biological activity. Region III indicates media that sample large quantities of proteins and retain biological activity and Region IV indicates media that sample large quantities of proteins but cannot retain activity. Among all the media tested, those which fall in Region III are most desired as liquefaction promoting media. It is clear that a small fraction of tested media fall in this category. Further, some of the most commonly used surfactants such as sodium dodecyl sulfate (SDS) and Span20 do not fall in this region. SDS induced significant reduction in biological activity and Span20 did not induce sufficient extraction. It is anticipated that the definition of boundaries between various regions will depend on the analyte of interest.

The effect of total surfactant concentration on protein solubilization was also tested. A 50:50 surfactant mixture of a Brij-30 and N-lauroyl sarcosine ranging from 0% to 2% (w/v) was formulated. After liquefaction of skin sample by ultrasound, supernatants were isolated from liquefied skin samples with centrifuge. The protein concentration of the samples was measured by using a colorimetric detection kit (Micro BCA Protein Assay Kit, Pierce). The calibration curve was obtained using freshly prepared Bovine Serum Albumin standards diluted in the Liquefaction Promoting Medium corresponding to the sample. Protein concentration was determined by dividing total protein content of the sample with tissue area.

The results are shown in FIG. 12.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method for generating a liquefied tissue sample from a subject in vivo, the method comprising:
- producing the liquefied tissue sample from the subject's tissue in vivo, the subject being a mammalian or non-mammalian animal, by:
  - applying energy to a desired skin surface location in the subject; and
  - applying a composition to the desired skin surface location in the subject, the composition comprising an anionic surfactant and a non-ionic surfactant in a ratio of about 3:1 to about 1:3 and a total surfactant concentration of about 1% (w/v); and
- collecting the liquefied tissue sample from the subject,
- the non-ionic surfactant comprising polyethylene glycol dodecyl ether; and
- the anionic surfactant comprising N-lauroyl sarcosine.

2. The method of claim 1, the composition comprising the anionic surfactant and the non-ionic surfactant in a ratio of about 1:1.

3. The method of claim 1, wherein the non-ionic surfactant consists essentially of polyethylene glycol (4) dodecyl ether.

4. The method of claim 1, wherein the applying energy comprises applying mechanical energy.

5. The method of claim 1, wherein the desired skin surface location in the subject comprises keratinized tissue.

6. The method of claim 1, further comprising collecting at least one analyte from the liquefied tissue sample.

7. The method of claim 6, wherein the analyte comprises a protein.

8. The method of claim 6, wherein the analyte comprises a cancer biomarker.

9. The method of claim 6, wherein the analyte comprises an antibody.

10. The method of claim 6, wherein the analyte comprises a peptide.

11. The method of claim 6, wherein the analyte comprises a lipid.

12. The method of claim 6, wherein the analyte comprises a nucleic acid.

13. The method of claim 6, wherein the analyte comprises a small molecule.

14. The method of claim 6, wherein the analyte comprises a microbe.

15. The method of claim 6, wherein the analyte comprises a warfare agent.

16. The method of claim 6, wherein the analyte comprises an environmental contaminant.

17. The method of claim 6, wherein the analyte comprises a drug.

18. The method of claim 1, further comprising:
   removing at least a portion of the liquefied tissue sample to leave an exposed area at the desired skin surface location in the subject; and
   applying a therapeutic composition to the exposed area at the desired skin surface location in the subject.

19. The method of claim 1, further comprising:
   removing at least a portion of the liquefied tissue sample to leave an exposed area at the desired skin surface location in the subject; and
   applying a cosmetic composition to the exposed area at the desired skin surface location in the subject.

* * * * *